US008257945B2

(12) United States Patent
Atabekov et al.

(10) Patent No.: US 8,257,945 B2
(45) Date of Patent: Sep. 4, 2012

(54) IDENTIFICATION OF EUKARYOTIC INTERNAL RIBOSOME ENTRY SITE (IRES) ELEMENTS

(75) Inventors: Joseph Atabekov, Moscow (RU); Yurii Dorokhov, Moscow (RU); Maxim Skulachev, Moscow (RU); Peter Ivanov, Moscow (RU); Yuri Gleba, München (DE)

(73) Assignee: Icon Genetics, Inc., Princeton, NJ (US)

( * ) Notice: Subject to any disclaimer, the term of this patent is extended or adjusted under 35 U.S.C. 154(b) by 1352 days.

(21) Appl. No.: 10/489,136

(22) PCT Filed: Sep. 3, 2002

(86) PCT No.: PCT/EP02/09844
§ 371 (c)(1),
(2), (4) Date: Mar. 16, 2004

(87) PCT Pub. No.: WO03/020928
PCT Pub. Date: Mar. 13, 2003

(65) Prior Publication Data
US 2005/0014150 A1    Jan. 20, 2005

(51) Int. Cl.
C12N 15/00 (2006.01)
C12N 15/09 (2006.01)
C12N 15/11 (2006.01)
C12N 15/63 (2006.01)
C12N 15/67 (2006.01)
C12N 15/82 (2006.01)
C12N 15/85 (2006.01)

(52) U.S. Cl. .................. 435/69.1; 424/24.1; 424/23.1; 435/320.1; 435/455

(58) Field of Classification Search .................. None
See application file for complete search history.

(56) References Cited

U.S. PATENT DOCUMENTS

| | | | |
|---|---|---|---|
| 5,139,812 A | 8/1992 | Lebacq | |
| 5,474,925 A | 12/1995 | Maliyakal et al. | |
| 5,576,198 A | 11/1996 | McBride et al. | |
| 5,627,059 A | 5/1997 | Capecchi et al. | |
| 5,670,623 A | 9/1997 | Shoseyov et al. | |
| 5,723,765 A | 3/1998 | Oliver et al. | |
| 5,877,402 A | 3/1999 | Maliga et al. | |
| 5,910,628 A | 6/1999 | Miller et al. | |
| 6,100,448 A | 8/2000 | Thompson et al. | |
| 6,146,845 A | 11/2000 | Kikly et al. | |
| 6,147,278 A | 11/2000 | Rogers et al. | |
| 6,174,700 B1 | 1/2001 | Haynes et al. | |
| 6,300,545 B1 | 10/2001 | Baszczynski et al. | |
| 6,331,416 B1 | 12/2001 | Shani et al. | |
| 6,331,661 B1 | 12/2001 | Baszczynski et al. | |
| 6,376,745 B1 * | 4/2002 | Atabekov et al. | 800/278 |
| 6,781,033 B2 | 8/2004 | Staub et al. | |
| 6,833,254 B2 | 12/2004 | Dasgupta et al. | |
| 2003/0049228 A1 * | 3/2003 | Santa-Cruz et al. | 424/93.2 |
| 2003/0188337 A1 | 10/2003 | Day et al. | |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |
| 2005/0014150 A1 | 1/2005 | Atabekov et al. | |
| 2005/0015829 A1 | 1/2005 | Koop et al. | |
| 2005/0015830 A1 | 1/2005 | Dorokhov et al. | |
| 2005/0059004 A1 | 3/2005 | Atabekov et al. | |
| 2005/0066384 A1 | 3/2005 | Klimyuck et al. | |
| 2005/0091706 A1 | 4/2005 | Klimyuck et al. | |
| 2006/0253924 A1 | 11/2006 | Turk et al. | |

FOREIGN PATENT DOCUMENTS
EP    0270 248    6/1988
(Continued)

OTHER PUBLICATIONS

Martinez-Salas E, Fernández-Miragall O. Picornavirus IRES: structure function relationship. Curr Pharm Des. 2004;10(30):3757-67.*
Stoneley M, Willis AE. Cellular internal ribosome entry segments: structures, trans-acting factors and regulation of gene expression. Oncogene. Apr. 19, 2004;23(18):3200-7.*
Parry et al. "Construction of a bidirectional promoter probe vector and its use in analyzing *nod* gene expression in *Rhizobium loti.*" *Gene*, 150: 105-109(1994).
Sanz et al. "Altered local and systemic spread of movement deficient virus in transgenic tobacco plants expressing the cucumber mosaic virus 3a protein" Arch Virol. 145:2387-2401 (2000).
Arnold et al. "Allelic Ladder, D18S51 Allele 8" EBI Database accession No. AAX01351 (Apr. 14, 1999) Abstract.
Bagwell, BC "Poly-dA 50mer Probe Target Sequence" EBI Database accession No. AAQ66922 (Jan. 24, 1995) Abstract.
Dorokhov et al. "Polypurine (A)-Rich Sequences Promote Cross-Kingdom Conservation of Internal Ribosome Entry" *PNAS* 99(8):5301-5306 (Apr. 16, 2002).
Lopez de Quinto et al. "Parameters Influencing Translational Efficiency in Aphthovirus IRES-Based Bicistronic Expression Vectors" *Gene* 217:51-56 (1998).

(Continued)

*Primary Examiner* — Maria Marvich
(74) *Attorney, Agent, or Firm* — Lerner, David, Littenberg, Krumholz & Mentlik, LLP

(57) ABSTRACT

A method of search for and identification of a eukaryotic IRES element active in cap-independent translation of RNA in eukaryotic cells is provided, comprising the following steps: i) screening eukaryotic mRNA sequences or corresponding DNA sequences for a potential IRES element having a block of nucleotides having: a) a length of at least 30 nucleotides; b) an adenine nucleotide content of at least 40 mol-%; and c) a pyrimidine nucleotide content of less than 40 mol-%; ii) inserting said potential IRES element into a linear dicistronic construct between an upstream gene and a downstream GUS reporter gene, whereby said potential IRES element is positioned for IRES-dependent translation of said downstream GUS gene and whereby said upstream gene is preceded by a stable hairpin structure to prevent IRES-independent translation of said genes; and iii) testing said potential IRES element for IRES-dependent translation of said GUS gene in a rabbit reticulocyte lysate or in a wheat germ extract in vitro translation assay, whereby GUS gene expression is quantitated preferably relative to a construct having a reference IRES element or a non-IRES element between said upstream gene and said GUS gene.

8 Claims, 14 Drawing Sheets

FOREIGN PATENT DOCUMENTS

| | | |
|---|---|---|
| EP | 1 045 037 | 10/2000 |
| WO | 87/00551 | 1/1987 |
| WO | 94/16089 | 7/1994 |
| WO | 95/34668 | 12/1995 |
| WO | 96/17954 | 6/1996 |
| WO | 98/09505 | 3/1998 |
| WO | 98/44097 | 10/1998 |
| WO | 98/54342 | 12/1998 |
| WO | 99/36516 | 1/1999 |
| WO | 99/25821 | 5/1999 |
| WO | 99/25855 | 5/1999 |
| WO | 01/11020 | 2/2000 |
| WO | 00/17365 | 3/2000 |
| WO | 00/20611 | 4/2000 |
| WO | 00/32799 | 6/2000 |
| WO | 00/68391 | 11/2000 |
| WO | 00/68431 | 11/2000 |
| WO | 00/70019 | 11/2000 |
| WO | 00/77174 | 12/2000 |
| WO | 00/77175 | 12/2000 |
| WO | 00/78985 | 12/2000 |
| WO | 0159138 A2 | 8/2001 |
| WO | WO 01/55369 | 8/2001 |
| WO | WO 01/59138 A2 | 8/2001 |
| WO | 01/81600 | 11/2001 |
| WO | 02/12522 | 2/2002 |
| WO | 02/29068 | 4/2002 |
| WO | 02/46438 | 6/2002 |
| WO | 02/46440 | 6/2002 |
| WO | 02/055651 | 7/2002 |
| WO | 02/057466 | 7/2002 |
| WO | 02/068664 | 9/2002 |
| WO | 02/077246 | 10/2002 |
| WO | 02/079481 | 10/2002 |
| WO | 02/088369 | 11/2002 |
| WO | 02/101060 | 12/2002 |
| WO | 03/001900 | 1/2003 |
| WO | 03/004658 | 1/2003 |
| WO | 03/020927 | 3/2003 |
| WO | 03/020928 | 3/2003 |
| WO | 03/020938 | 3/2003 |

OTHER PUBLICATIONS

International Search Report for application No. PCT/EP02/09844, mailed Jul. 15, 2003.
Donson et al. "Systemic expression of a bacterial gene by a tobacco mosaic" *Proc. Natl. Acad. Sci. USA* 88: 7204-7208 (1991).
Murakami et al. "High-level expression of exogenous genes by replication competent retrovirus vectors with an internal ribosomal entry site" *Gene 202*: 23-29 (1997).
Derbyshire et al. "Lightning strikes twice: Intron-intein coincidence" *Proc. Natl. Acad. Sci. USA* 95:1356-1357 (1998).
Lustig et al. "Long Poly(A) Tracts in the Human Genome are Associate with the *Alu* Family of Repeated Elements" *J. Mol. Biol.* 180:753-759 (1984).
Wu et al. "Markerless Deletions of *pil* Genes in *Myxococcus xanthus* generated by Counterselection with the *Bacillus subtilis sacB* Gene" *Journal of Bacteriology* 178(19):5817-5281 (1996).
Hagemann et al. "Extranuclear Inheritance: Plastid Genetics" *Progress in Botany*, vol. 55, 260-275 (1994).
Klaus et al. "Generation of Marker Free Plastid Transformants Using a Transiently Cointegrated Selection Gene" *Nature Biotechnology* 22: 225-229 (2004).
Mühlbauer et al. "Functional analysis of plastid DNA replication origins in tobacco by targeted inactivation" *The Plant Journal*, 32:175-184 (2002).
Ruf et al. "Stable Genetic Transformation of Tomato Plastids and Expression of a Foreign Protein in Fruit" *Nature Biotechnology* 19: 870-875 (2001).
Shimada et al. "Fine Structural Features of the Chloroplast Genome: Comparison of the Sequenced Chloroplast Genomes" *Nucleic Acids Research* 19: 983-995 (1991).
Shinozaki et al. "The Complete Nucleotide Sequence of the Tobacco Chloroplast Genome: Its Gene Organization and Expression" *The EMBO Journal* 5: 2043-2049 (1986).
Sidorov et al. "Stable Chloroplast Transformation in Potato: Use of Green Fluorescent Protein as a Plastid Marker" *The Plant Journal* 19: 209-216 (1999).
Cornelis et al., Molecular Cell, 5; 597-605 (2000).
Gaille et al, The tobacco etch viral 5' leader and poly(A) tail are functionally synergistic regulators or translation, Gene, 1995, vol. 165. pp. 233-238.
Bergamini et al, Picornavirus IRESes and the poly(A) tail jointly promote cap-independent translation in a mammalian cell-free system. RNA 2000 6:1781-1790.
Iizuka et al, Cap-Dependent and Cap-Independent Translation by Internal Initiation of mRNAs in Cell Extracts Prepared from *Saccharomyces cerevisiae*, Molecular and Cellular Biology, Nov. 1994, p. 7322-7330.
Karpova et al, The 3'-untranslated region of brome mosaic virus RNA does not enhance translation of capped mRNAs in vitro, FEBS Letters 360 (1995) 281-285.
Attal et al., "The efficiency of different IRESs (Internal Ribosomes Entry Site) in monocistronic mRNAs," *Molecular Biology Reports* 27: 21-26 (2000).
Skulachev et al., "Internal Initiation of Translation Directed by the 5'-Untranslated Region of the Tobamovirus Subgenomic RNA $I_2$," *Virology* 263: 139-154 (1999).
Albert et al. (1995) "Site-specific integration of DNA into wild-type and mutant lox sites placed in the plant genome" The Plant Journal 7:649-659.
Allison et al., "Deletion of rpoB Reveals a Second Distinct Transcription System in Plastids of Higher Plants," The EMBO Journal, 15:11 2802-2809 (1996).
Altschul et al. "Basic Local Alignment Search Tool," J. Mol. Biol., 215:403-410 (1990).
Anandalakshmi et al. (1998) "A viral suppressor of gene silencing in plants" Proc. Natl. Acad. Sci. U.S.A. 95:13079-13084.
Anandalakshmi et al. (2000) "A calmodulin-related protein that suppresses posttranscriptional gene silencing in plants" Science 290:142-144.
Bateman et al. (2000) "Tools for chloroplast transformation in *Chlamydomonas*: expression vectors and a new dominant selectable marker" Mol. Gen. Genet. 263:401-410.
Bergamini et al. "Picornavirus IRESes and the Poly(A) tail Jointly Promote Cap-Independent Translation in a Mammalian Cell-free System," RNA, 6:1781-1790 (2000).
Bogorad, Lawrence, "Engineering Chloroplasts: an Alternative Site for Foreign Genes, Proteins, Reactions and Products," TIBTECH, 18:257-263 (Jun. 2000).
Bouchez et al. (1993) "A binary vector based on Basta resistance for in planta transformation of *Arabidopsis thaliana*" C. R. Acad. Sci. Paris, Science de la vie 316:1188-1193.
Boynton et al., "Chloroplast Transformation in *Chlamydomonas* with High Velocity Microprojectiles," Science, 240:1534-1538 (1988).
Carpin et al. (2001) "Identification of a Ca2+-Pectate Binding Site on an Apoplastic Peroxidase" The Plant Cell 13:511-520.
Chappell et al. "A 9-nt Segment of Cellular mRNA Can Function as an Internal Ribosome Entry Site (IRES) and When Present in Linked Multiple Copies Greatly Enhances IRES Activity," PNAS, 97(4):1536-1541 (Feb. 15, 2000).
Clelland et al. (1999) "Hiding Messages in DNA Microdots," Nature 399:533-534.
Coutts et al. "Development of Geminivirus-based Gene Vectors for Dicotyledonous Plants" Australian Journal of Plant Physiology 17:365-375 (1990).
Dale et al. "Intra- and intermolecular site-specific recombination in plant cells mediated by bacteriophage P1 recombinase" Gene 91:79-85 (1990).
Dale et al. "Mutations in the CRE/LOX Recombination Site Enhance the Stability of Recombination Products: Applications for Gene Targeting in Plants" Journal of Cellular Biochemistry 50 (S16S):206 (1992).
Daniell, "New Tools for Chloroplast Genetic Engineering," Nature Biotechnology, 17:855-856 (Sep. 1999).
De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).

Domingo et al. (1999) "Identification of a novel peptide motif that mediates cross-linking of proteins to cell walls" The Plant Journal 20:563-570.

Drescher et al., "The Two Largest Chloroplast Genome-Encoded Open Reading Frames of Higher Plants are Essential Genes", The Plant Journal, 22(2):97-104 (2000).

El-Sheekh, M.M. (2000) "Stable Chloroplast Transformation in *Chlamydomonas reinhardtii* using Microprojectile Bombardment" Folia Microbiol. 45(6) 496-504.

Fischer et al., "Selectable Marker Recycling in the Chloroplast," Mol. Gen. Genet., 251:373-380 (1996).

Gatz et al. (1991) "Regulation of a modified CaMV 35S promoter by the Tn10-encoded Tet repressor in transgenic tobacco" Mol. Gen. Genet. 227:229-237.

Hager at al., "Enslaved Bacteria as New Hope for Plant Brotechnologists," Appl. Microbial. Biotechnol., 54:302-310 (2000).

Heifetz, Peter B., "Genetic Engineering of the Chloroplast," Biochimie, 82:655.666 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IRESs): Reality and Use" Transgenic Research, 8:157-177 (1999).

Iamtham et al. (2000) "Removal of antibiotic resistance genes from transgenic tobacco plastids" 18:1172-1176.

Ivanov et al. "A Tobamovirus Genome That Contains an Internal Ribosome Entry Site Functional In Vitro," Virology, 232:32-43 (1997).

Jeon et al. (2000) "T-DNA insertional mutagenesis for functional genomics in rice" Plant J. 22:561-570.

Kofer et al., "PEG-Mediated Plastid Transformation in Higher Plants," In Vitro Cell. Dev. Biol.—Plant, 31:303-309 (1998).

Koshinsky et al. (2000) "Cre-lox site-specific recombination between *Arabidopsis* and tobacco chromosomes" The Plant Journal 23:715-722.

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed Immobilization of recombinant staphylococci on cotton fibers by functional display of a fungal cellulose-binding domain" FEMS Microbiology Letters 195:197-204.

Martinez-Salas, Encarnacion. "Internal Ribosome Entry Site Biology and Its Use In Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure in Poly(A)-tail-promoted Translation in Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat x Tripsacum Crosses" Crop Science 33:973-976.

Ruf et al., "Targeted inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of *Saccharomyces cerevisiae*" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170 (1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in *Chlamydomonas* chloroplasts " Plant J. 11:635-648.

Suzuki et al., "Engineering of the rp123 Gene Cluster to Replace the Plastid RNA Polymerase α Subunit with the *Escherichia coli* Homologue," Curr. Genet., 38:218-225 (2000).

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in *Arabidopsis thaliana* by transient expression of cre" Plant Molecular Biology 38:393-406 (1998).

Urwin et al. (2000) "Functional characterization of the EMCV IRES in plants" Plant J. 24:583-589.

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

Fowlks et al, Detection and Sequence of an Internal A-Rich T1 Oligonucleotide Series in Brome Mosaic Viral RNA3, FEBS Letters, Jul. 1981 pp. 32-38.

NCBI Sequence resulté for GenBank Mo. No. AZ342739, www.ncbi.nlm.nih.gov/entrez/viewer.fcgi?db=nucgss&id=10420275 <http://www.ncbi.nlm.nih.gov/entrez/viewer.fcgi?db=nucgss&id=10420275>, Sep. 29, 2000, pp. 1-2.

Product information for *E.coli* Ki 2 ER2420/pBeloBAC1 1, New England BioLabs Catalog #4154S. printed Aug. 2, 2007, pp. 1-2.

NCBI Sequence results for GenBank Acc. No. AQ304254, www.ncbi.nlni.nih.gov/entrez/viewer.fcgi?dbrnucgss&id4021052, Dec. 15, 1999, pp. 1-2.

Mahairas CC, Wallace JC, Smith K, Swartzell 5, Holzman T, Keller A, Shaker R, Furlong J, Young J, Zhao 5, Adams MD, Hood. 1999. Sequence-tagged connectors: a sequence approach to mapping and scanning the human genome. Proc Natl Acad Sci USA. Aug. 17, 1999;96(17):9739-44.

Alberts B, Bray D, Lewis J, Raff M, Roberts K, and Watson J. 1994. Molecular biology of the cell, 3rd Ed. Garland Publ. Inc., U New York, pp. 58-59.

Smith, A. 1997.Oxford Dictionary of Biochemistry and Molecular Biology, Oxford University Press, USA. pp. 34, 131 and 426.

Kozak, "Initiation of Translation in Prokaryotes and Eukaryotes" Gene 234:187-208 (1999).

Lopez de Quinto et al. "Parameters Influencing Translational Efficiency in Aphthovirus IRES-Based Bicistronic Expression Vectors" Gene 217:51-56(1998).

Arnold et al. "Allelic Ladder D18551 Allele 8" EMBL Database Accession No. AAXO1351 (Apr. 14, 1994).

Bagwell et al. "Poly-dA 50mer Probe Target Sequence" EMBL Database Accession No. AA066922 (Jan. 24, 1995).

Dorokhov et al. "Polypurine (A)-rich Sequences Promote Cross-kingdom Conservation of Internal Ribosome Entry," PNAS, 99(8):5301-5306 (Apr. 16, 2002).

Owens et al. Identification of Two Short Internal Ribosome Entry Sites Selected From Libraries of Random Oligonucleotides, PNAS, 98(4): 1471-1476 (Feb. 13, 2000).

* cited by examiner

A. Nucleotide sequence of NtHSF-1 mRNA 5'leader (EMBL accession code AB014483):

ggcacgaggc tcccattaat atttctctct cttgtaatt ccattattct gtagtagatt cacgtccgag tttaangaag agagaaaact gaaaaggcag aaaattccag agctttagat
ttagccaaag atagttatgg tcgttgtt cttggtgaag attggcaaag taggagccaa tgaaagaaac taagatcata atcaatcgcc ccaaaaacaa cctttgttcat tctatgttt
ttctcttcgg ttttctatgtt tgggattggg aattcctcac tgtccttttg cttttcagtt atgctcctt ctaattttcc ctagctagga tctctcaat taattccct tttcatttc
aactaactca taattagcc aaagttca aagagtttg tgtaacgttta tagacgttta gagaaacagg ggaaaacagg gaaaaacaa ggg ATG B. To produce pH-GFP-NtHSF-GUS plasmid PCR fragment was obtained using primers aagtaagcttggcacgaggctcccattaatatttc and
ggaccatgcttgttttcccctgtatttctctg and total genomic DNA extracted from Nicotiana tabacum Samsun NN.

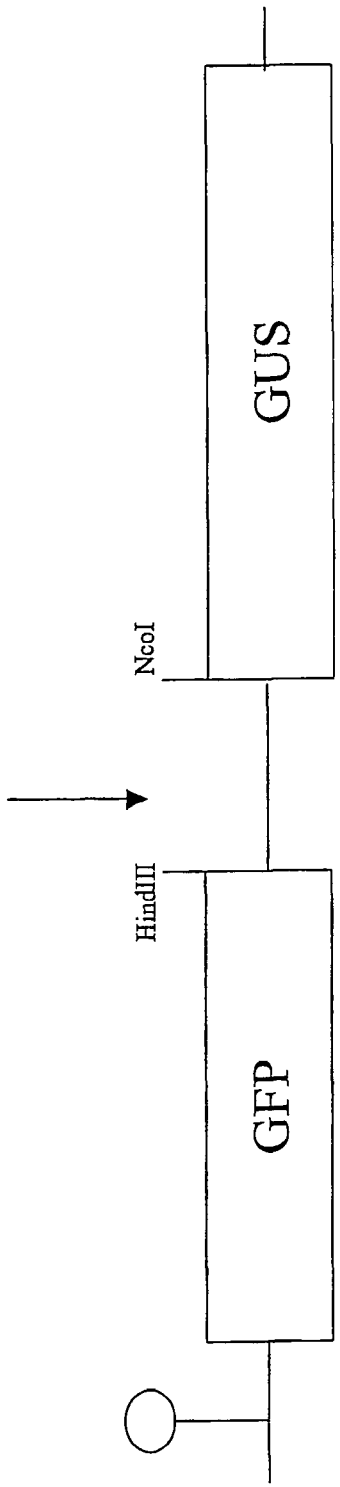

Obtained PCR product was cloned into pH-GFP-IRES$_{CP148}$-GUS using HindIII and NcoI sites. Resulting plasmid contained 5'-untranslated region of NtHSF-1 RNA (with introduced HidnIII and NcoI sites) cloned between GFP and GUS genes.

Fig. 3

AC: U68093, Human poly(A)-binding protein (PABP) gene.
ccttctcccc ggcggttagt gctgagagtg cggagtgtgt gctccgggct cggaacacac
atttattatt aaaaaatcca aaaaaaatct aaaaaaatct tttaaaaaac cccaaaaaaa
tttacaaaaa atccgcgtct cccccgccgg agacttttat ttttttttctt cctcttttat
aaaataaccc ggtgaagcag ccgagaccga cccgcccgcc cgcggccccg cagcagctcc
aagaaggaac caagagaccg aggccttccc gctgcccgga cccgacaccg ccaccctcgc
tccccgccgg cagccggcag ccagcggcag tggatcgacc ccgttctgcg gccgttgagt
agttttcaat tccggttgat ttttgtccct ctgcgcttgc tccccgctcc cctcccccg
gctccggccc ccagcccgg cactcgctct cctcctctca cggaaaggtc gcggcctgtg
gccctgcggg cagccgtgcc
gag ATG

AC: D85730, HSP70, testis variant.
gacggggtgg ggggtggggg gaccccggtt gtgcagtttg atattgaggg agcccccacc
tactcgctgg ggctgcgtaa tctgtacgct tccaaactga agcgaaggcg
tcgggagactb aggcctcaga gaacc ATG

AC:U15590. HSP 17 KD protein 3 (HSPB3)
gcattccgtg ctatgattca ggcctaatta agtgattgcg tctgggcacg gctataaacc
actagctgct tcaactggta atccagtcag taggcaactg caggggctcg ccactgactg
aaggcagtgg aaggttggca gaaggaggct gttcaagget gttttttgcct tcact ATG

AC: Y17782, HSP B3
ttaagtgatt gcgtctgggc acggctataa accactagct gcttcaactg gtaatccagt
cagtaggcaa ctgcaggggc tcgccactga ctgaaggcag tggaaggttg gcagaaggag
gctgttcaag gctgtttttg ccttcact
ATG

AC: AJ277242 HSPHDJ2
gggaaacagg caattaaaga gggtggagca ggtggcggtt ttggctcccc catggacatc
tttgatatgt tttttggagg aggaggaagg atgcagagag aaaggagagg taaaaatgtt
gtacatcagc tctcagtaac cctagaagac ttatataatg gtgcaacaag aaaactggct
ctgcaaaaga atgtgatttg tgacaaatgt gaaggtagag gaggtaagaa aggagcagta
gagtgctgtc ccaattgccg aggtactgga ATG

AC: D87666, HSP 90
gccagcgcag gggcttctgc tgaggggca ggcggagctt gaggaaaccg cagataagtt
tttttctctt tgaaagatag agattaatac aactacttaa aaaatatagt caataggtta
ctaagatatt gcttagcgtt aagtttttaa cgtaatttta atagcttaag attttaagag
aaaatatgaa gacttagaag agtagcatga ggaaggaaaa gataaaaggt ttctaaaaca
tgacggaggt tgagatgaag cttcttcatg gagtaaaaaa tgtatttaaa
agaaaattga
gagaaaggac tacagagccc cgaattaata ccaatagaag ggcaatgctt ttagattaaa
atgaaggtga cttaaacagc ttaaagttta gtttaaaagt tgtaggtgat taaaataatt
tgaaggcgat cttttaaaaa gagattaaac cgaaggtgat taaagacct tgaaatccat
gacgcaggga gaattgcgtc atttaaagcc tagttaacgc atttactaaa cgcagacgaa
aatggaaaga ttaattggga gtggtaggat gaaacaattt ggagaagata gaagtttgaa
gtggaaaact ggaagacaga agtacgggaa ggcgaagaaa agaatagaga agatagggaa
attagaagac tttagtgtca gtcaccaaag aaggcctgga
acttccagag gatgaagaag agaaaaagaa gcaggaagag aaaaaaacaa agtttgagaa
cctctgcaaa atc ATG

Fig. 7

AC: 13229, HSP70B

```
gcgtgaagag  ctgcagtgtc  actcttaaag  ctgaattaat  ctctgccatt  ccttaaggaa
acaggcaact  gtcttaaaac  cgtggtttgg  aaaatatttt  gttcaagata  aaactgtttt
aagatatatg  tatatatatc  ttatatatct  gtattcgcat  ggtaacatat  cttcggtctt
cctgccgctg  ggctctcagc  ggccctccaa  ggcagcccgc  aggcccgtgc  tcgcctcagg
gatcctccac  agccccgggg       agaccttgcc       tctaaagttg       ctgcttttgc
agctctgcca
caaccgcgcg  tcctcagagc  cagccgggag  gagctagaac  cttccccgcg  tttctttcag
cagccctgag  tcagaggcgg  gctggccttg  caagtagccg  cccagccttc  ttcggtctca
cggaccgatc  cgcccgaacc  ttctcccggg  gtcagcgccg  cgctgcgccg  cccggctgac
tcagcccggg  cgggcgggcg  ggaggctctc  gactgggcgg  gaaggtgcgg  gaaggttcgc
ggcggcgggg  tcggggaggt  gcaaaggat   gaaaagcccg  tggacggagc  tgagcagatc
cggccgggct  ggcggcagag  aaaccgcagg  gagagcctca  ctgctgagcg  cccctcgacg
cgggcggcag  cagcctccgt  ggcctccagc  atccgacaag  aagcttcagc     c ATG
```

AC: M9627, HSP86

```
aattaatttt  gattacattt  aaaattctat  atggcaaaaa  taccataatt  aaagataaaa
ggcaaagaac  aaattgggaa  aaatattttt  caacatatat  aaccaagggc  taatttctct
aacacctaaa  aagttcttat  aaatcaataa  aaagaaaacc  aacatctcaa  tggaaaaaga
acaaagctca  taaagagttc  atagaaaaag  gatatacaaa  tggctttaaa  catgtgaaag
aatgttcaac  ttcactcaca  ataagaaaaa  atacaaatta  tgagttgctt  cagcatcctg
gtgttgctgt  gccgtgggtc  ctgtgcggtc  acttagccaa        g ATG
```

Fig. 7 (continued)

AC: U94192, tobacco 48-kD MAP kinase
cacaattcca catattcatt gacatactac ggcccttctt ccctaattt
aagacaaagg aaaaaaagta attattgatt cttctaggat ttacaattt
tgttgacgaa ttttccaaaa aaaaaaat ATG

AC: AF165186, tobacco MAP kinase
ggcacgaggc aatttcagtt gtgatctttc atgatttcca taaaagagtg
agctttagca agaatacaga aaccccagt tgccaagaag caatttttac
tgtggttttt caagatttag ct ATG

AC: AJ250174, N.tabacum GTP-binding protein (rac gene)
aaaaaaaaaa aaaaaaaaaa aaaaaaaaaa aaaagaaaaa agaaaaaa ATG

AC: AB029508, Oryza sativa GTP-binding protein OsRac1
gtgagagtga acaagagata agctaagcta gtacagcaac cagcaagaac
aaagaagagt ggccggagtg ggcggggag ATG

AC: AF190655, N.tabacum poly(A)-binding protein (PABP) mRNA
cgttgctgtc ggagattttg tatctgcgaa taaaaagagg agagggaagt
aaacaaaaaa atcggaaaaa gtttgaaaaa gaaattatc tttattattt
tttttttgtg ttgatttgag ATG

PLANT HEAT SHOCK PROTEINS mRNA 5'UTR

AC: AB017273,
gaaattgaaa ggattattgc ataagaaaag ctaagatcgt cacttcaaaa
ATG

AC: AF005993,
tcgaaatcag agagggcaa agcaaatcgc accaggcaaa ctcagagggt
cttccggcga accccaaagc gagagagcga gcgagcgatt cccaggagag
gagaggaggc ggag ATG

AC: AF035460,
ccacaacagc gaaggagaaa gcagaccaac ctagccaccc agggagaaag
aggccaaaag ggaggggaga gtgtcgtc ATG

AC: AF074969,
ggatccccca attctggttt ttgacctggg gaggaggcac ctttgatgtt
tcagttctcg aagttggtga tggtgttttt gaggtgctgt ctacatctgg
tgatactcac ccttggtggt gatgactttg acaagagaat tgttgattgg
ctggctggaa gcttcaagaa tgatgagggt attgacctgc taaaagacaa
gcaagctctc cagactgtct tacagaagca gctgagaagg ccaag ATG

Fig. 8

AC: AF087640
gatcggattg agtgatacga cttgtggagt gttggttcgt ggcatgcgcg
ttgtcgaaag agtggttgca ggcgatatcg cagtggggac tcgggttttt
tcaattctct cgtggagttc gttcgtccag ctgatcgctc ccgacgcttg
tgggttgtag ctcgggtggc attgcggtcg aggttggtga gggtgatcgc
tgggtggagc gcattgtcga ggagcggaga ggtaggc ATG

AC: AF133840,
ggcacgagag aaaaactagc cgaagcaaac ccattccaca agcacctggt
gggatcatct catcatcaga aacaaagaga gagattccgt gcccacttgt
tgtagtagat tgtgaggatt gaggagtagc aaagagaagc agcc ATG

AC: AF174433,
ggcacgagag aaaaactagc cgaagcaaac ccattccaca agcacctggt
gggatcatct catcatcaga aacaaagaga gagattccgt gcccacttgt
tgtagtagat tgtgaggatt gaggagtagc aaagagaagc agcc ATG

AC: AF208051,
tttaaccagt tcataagaaa gaggaaagat aagtaattaa ta ATG

Fig. 8 (continued)

To produce pH-GFP-PABP-GUS plasmid PCR fragment was obtained using primers gcggCAAGCTTcgttgctgtcgtcggagattttgtatc (HindIII site underlined) and cgcgCCATGGcaaatcaacacacaaaaaacaaaaaaacaaaaaaaataataaag (NcoI site underlined) and total genomic DNA extracted from *Nicotiana tabacum* Samsun NN.

Obtained PCR product was cloned into pH-GFP-IRES$_{CP'148}$-GUS using HindIII and NcoI sites. Resulting plasmid contained 5'-untranslated region of NtHSF-1 RNA (with introduced HindIII and NcoI sites) cloned between GFP and GUS genes.

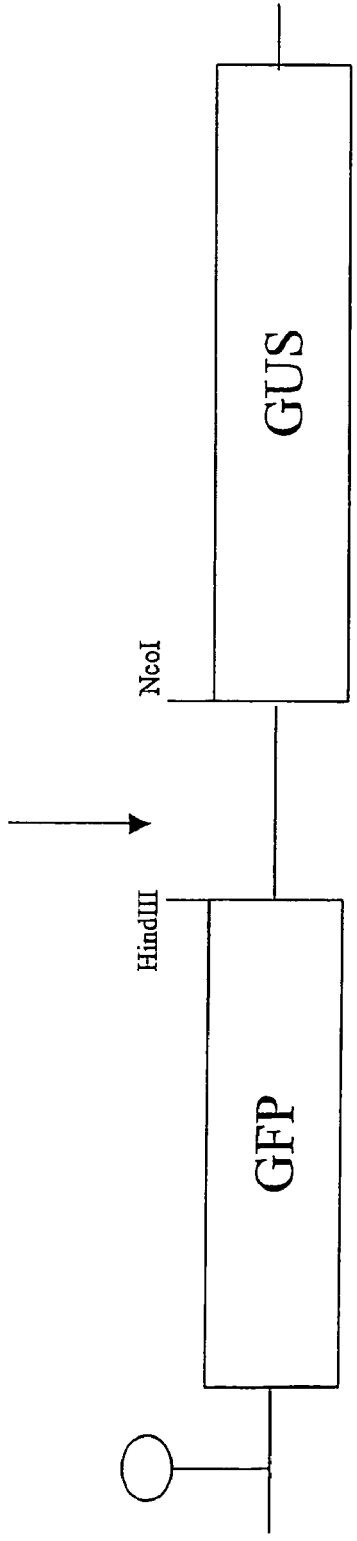

Fig. 9

To produce pH-GFP-48K MAPK-GUS plasmid PCR fragment was obtained using primers gcggCAAGCTTcacaattccacatattcattg (HindIII site underlined) and cgcgCCATGGtttttttttggaaaattcgtc (NcoI site underlined) and total genomic DNA extracted from *Nicotiana tabacum* Samsun NN.

Obtained PCR product was cloned into pH-GFP-IRES<sub>CP'148</sub>-GUS using HindIII and NcoI sites. Resulting plasmid contained 5'-untranslated region of 48K MAPK RNA (with introduced HidnIII and NcoI sites) cloned between GFP and GUS genes.

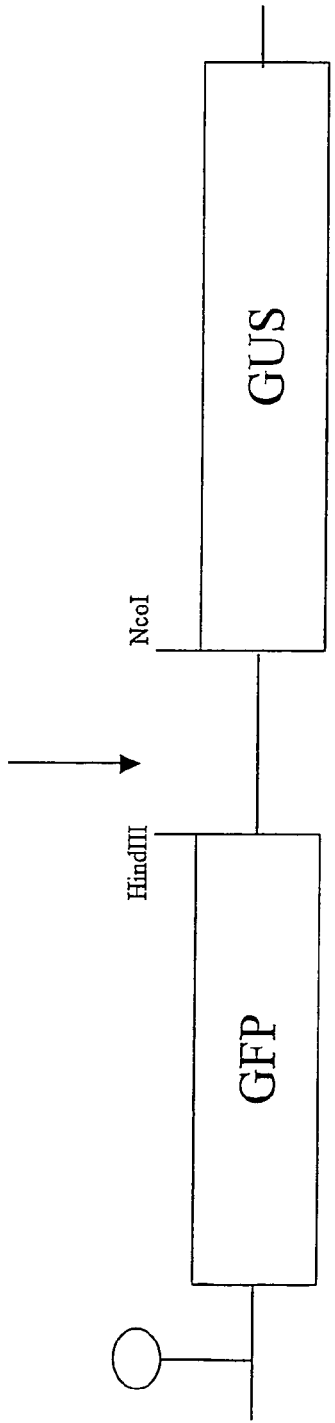

Fig. 10

EMCV IRES-containing mRNA 5'UTR:
```
     ttgaaagccg ggggtgggag atccggattg ccagtctact cgatatcgca ggctgggtcc  60
     gtgactaccc actcctactt tcaacgtgaa ggctacgata gtgccagggc gggtactgcc 120
     gtaagtgcca cccaaccaa caaaacaaaa acccccccc ccccccccc ccccccccc 180
     ccccccccc ccccccccc ccccccccc ccccccccc ccccccccc ccccccccc 240
     ccccccccc ccccccccc cccccccca acgttactgg ccgaagccgc ttggaataag 300
     gccggtgtgc gtttgtctat atgttatttc taccacatca ccgtcttttg gtggtgtgag 360
     ggcccggaac ctggccctgt cttcttgacg agcattccta ggggtctttc ccctctcgcc 420
     aaaggaatgt aaggtctgtt gaatgtcgtg aaggaagcag ttcctctgga agcttcttga 480
     agacaagcaa cgtctgtagc gaccctttgc aggcagcgga aatccccacc tggtaacagg 540
     tgcctctgcg gccaaaagcc acgtgtataa gatacacctg caaaggcggc acaaccccag 600
     tgccacgttg tgagttggat agttgtggaa agagtcaaat ggctcacctc aagcgtattc 680
     aacaagggc tgaaggatgc ccagaaggta ccccattgta tgggatctga tctggggcct 740
     cggtgcacgt gctctacacg tgttgagtcg aggttaaaaa acgtctaggc ccccgaacc 820
     acggggacgt ggttttcctt tgaaaaccac gattgtaaga tggctacaac tatgaacaa 880
     gagatttgtg cgcattccct cacgtttaaa ggatgcccga a ATG
```

Poliovirus IRES-containing mRNA 5'UTR:
```
     ttaaaacagc tctggggttg ttcccacccc agaggcccac gtggcggcta gtacactggt  60
     atcacggtac ctttgtacgc ctgttttata ctccctcccc cgcaacttag aagcatacaa 120
     ttcaagctca ataggagggg gtgcaagcca gcgcctccgt gggcaagcac tactgtttcc 180
     ccggtgaggc cgcatagact gttcccacgg ttgaaagtgg ccgatccgtt atccgctcat 240
     gtacttcgag aagcctagta tcgctctgga atcttcgacg cgttgcgctc agcactcaac 300
     cccggagtgt agcttgggcc gatgagtctg acagtcccc actggcgaca gtggtccagg 360
     ctgcgctggc ggcccacctg tgcccaaag ccacgggacg ctagttgtga acagggtgtg 420
     aagagcctat tgagctacat gagagtcctc cggcccctga atgcggctaa tcctaaccat 480
     ggagcaggca gctgcaaccc agcagccagc ctgtcgtaac gcgcaagtcc gtggcggaac 540
     cgactacttt ggtgtccgt gtttccttt attcttgaat ggctgcttat ggtgacaatc 600
     atagattgtt atcataaagc gagttggatt ggccatccag tgtgaatcag attaattact 660
     cccttgtttg tggatccac tcccgaaacg ttttactcct taacttattg aaattgtttg 720
     aagacaggat ttcagtgtca ca ATG
```

Hepatitis C virus IRES-containing mRNA 5'UTR:
```
     ggtcatcttg gtagccacta taggtgggtc ttaagggttg gtcaaggtcc ctctggcgct  60
     tgtggcgaga aagcgcacgg tccacaggtg ttgccctac cggtgtgaat aagggcccga 120
     cgtcaggctc gtcgttaaac cgagccatt acccacctgg gcaaacaacg cccacgtacg 180
     gtccacgtcg ccctacaatg tctctcttga ccaataggct ttgccggcga gttgacaagg 240
     accagtgggg gctgggcggc ggggaagga cctccgtcgc tgcccttccc ggtgggtgg 300
     gaaatgcatg gggccaccca gctccgcggc ggcctgcagc cggggtagcc caananccctt 360
     cgggtgaggg cgggtggcat ttttctttcc tataccgatc ATG
```

Insect RNA virus (Plautia stali intestine virus, PSIV) IRES:
```
acccucgugc ucgcucaaac auuaaguggu guugugcgaa aagaaucuca cuu CAA
```

Homo sapiens apoptotic protease activating factor 1 (Apaf-1)
IRES-containing mRNA 5'UTR:
```
     aagaagaggt agcgagtgga cgtgactgct ctatcccggg caaaagggat agaaccagag  60
     gtggggagtc tgggcagtcg gcgaccgcg aagacttgag gtgccgcagc ggcatccgga 120
     gtagcgccgg gctccctccg gggtgcagcc gccgtcgggg aagggcgcc acaggccggg 180
     aagacctcct cccttttgtgt ccagtagtgg ggtccaccgg agggcggccc gtgggccggg 240
     cctcaccgcg gcgctccggg actgtgggt caggctgcgt tgggtggacg cccacctcgc 300
     caaccttcgg aggtccctgg gggtcttcgt gcgcccggg gctgcagaga tccaggggag 360
     gcgcctgtga ggcccggacc tgccccgggg cgaagggtat gtggcgagac agagccctgc 420
     accctaatt cccggtggaa aactcctgtt gccgtttccc tccaccggcc tggagtctcc 480
     cagtcttgtc ccggcagtgc cgccctcccc actaagacct aggcgcaaag gcttggctca 540
     tggttgacag ctcagagaga gaaagatctg agggaag ATG
```

Fig. 11

Human c-myc IRES-containing mRNA 5'UTR:
```
    ctgctcgcgg ccgccaccgc cgggcccgg ccgtccctgg ctccctcct gcctcgagaa   60
    gggcagggct tctcagaggc ttggcgggaa aaagaacgg agggagggat cgcgctgagt  120
    ataaaagccg gttttcgggg ctttatctaa ctcgctgtag taattccagc gagaggcaga  180
    gggagcgagc gggcggccg ctagggtgga agagccggc gagcagagct gcgctgcggg  240
    cgtcctggga agggagatcc ggagcgaata gggggcttcg cctctggccc agccctcccg  300
    cttgatcccc caggccagcg gtccgcaacc cttgccgcat ccacgaaact ttgcccatag  360
    cagcgggcgg gcactttgca ctggaactta caacacccga gcaaggacgc gactctcccg  420
    acgcggggag gctattctgc ccatttgggg acacttcccc gccgctgcca ggaccgctt   480
    ctctgaaagg ctctccttgc agctgcttag acgctggatt tttttcgggt agtggaaaac  540
    cagcagcctc ccgcgacgat gcccctcaac gttagcttca ccaacaggaa ctatgacctc  600
    gactacgact cggtgcagcc gtatttctac tgcgacgagg aggagaactt ctaccagcag  660
    cagcagcaga gcgagctgca gccccggcg cccagcgagg atatctgaa gaaattcgag  720
    ctgctgccca ccccgcccct gtccctagc cgccgctccg ggctctgctc gccctcctac  780
    gttgcggtca cacccttctc ccttcgggga gacaacgacg gcggtggcgg gagcttctcc  940
    acggccgacc agctggag ATG
```

Human BiP IRES-containing 5'UTR 5'UTR:
```
    aggtcgacgc cggccaagac agcacagaca gattgaccta ttggggtgtt tcgcgagtgt   60
    gagagggaag cgccgcggcc tgtatttcta gacctgccct tcgcctggtt cgtggcgcct  120
    tgtgaccccg ggcccctgcc gcctgcaagt cggaaattgc gctgtgctcc tgtgctacgg  180
    cctgtggctg gactgcctgc tgctgcccaa ctggctggca ag ATG
```

Homo sapiens eIF4GII IRES-containing mRNA 5'UTR:
```
    caatcccaca gagtattgat gaggaaactg aagtttggag cgatcacatc attttcccaa   60
    ggtaacacaa gtggcaagac agccgggaac ccctacccca tccccttatt cagcacatga  120
    aataaacaag gggcatccaa atcttgcggc aacgccccg ggacatgcat cgtccctgg   180
    actctctcaa accccttatc cctctggaca gaatgcaggt ccaaccacgc tggtataccc  240
    tcaaacccct cagaca ATG
```

Rattus norvegicus fibroblast growth factor 2 IRES-containing mRNA 5'UTR:
```
                  gcggggc gcgcggggcc ggggtgcagg cggggacgcg gggtgacgc    48
    gggcccggc cgctgtagca cacaggggct cggtctctcg gcttcaggcg gagtccggct  108
    gcactaggct gggagcgcgg cgggacgcga accgggaggc tggcagcccg cgggcgagcc  168
    gcgctggggg gccgaggccg gggtcgggc cggggagccc cgagagctgc cgcagcgggg  228
    tcccggggcc gcggagggc c ATG
```

Homo sapiens vascular endothelial growth factor C IRES:
```
                                  ggcactggc tgggagggcg ccctgcaaag ttgggaacgc  960
    ggagccccgg acccgctccc gccgcctccg gctcgccag gggggtcgc cgggaggagc 1020
    ccgggggaga .gggaccagga ggggcccgcg gcctcgcagg ggcgccgcg ccccaccc  1080
    tgccccgcc agcggaccgg tccccaccc ccggtccttc cacc ATG
```

Rattus norvegicus X-linked inhibitor of apoptosis (riap3) IRES:
```
    gtcaggctct ggcttggagc tggggaggcg gggtgggggg gtggggggg tcggctgca   60
    taatgaggac tgggggtttt ttggatgccc ccttccggct ccgcgagacg gcggaccttg  120
    gcggtccccc gagcgagcgc gacgctaatc gagggctgct cggctcgaga ggccggggcc  180
    cgccgcccag cagagttgtg ttttcctga tcggggctcg ggccgcccct cctccgggac  240
    cctcccctcg gaaccgtcg cccgcggcgg ttagttagga ctggattgct tggcgcgaaa  300
    aggtggacaa gtcgtatttt caagagaag ATG
```

Gtx homeodomain protein 5'UTR IRES:
```
    cccgagccgg cgggugcggg cgguggcagc ggggcccgga ugggcgcccg g  51
```

Fig. 11 (continued)

SEQUENCE LISTING

<160> NUMBER OF SEQ ID NOS: 44

<210> SEQ ID NO 1
<211> LENGTH: 64
<212> TYPE: DNA
<213> ORGANISM: Artificial
<220> FEATURE:
<223> OTHER INFORMATION: Reference IRES element -continued

```
<400> SEQUENCE: 1
gaaagaaaga aagaaagaaa gaaagaaaga agaaagaaaa gaaagaaaga aagaaagaaa    60
gaaa                                                                 64

<210> SEQ ID NO 2
<211> LENGTH: 66
<212> TYPE: DNA
<213> ORGANISM: Artificial Sequence
<220> FEATURE:
<223> OTHER INFORMATION: Hairpin structure sequence

<400> SEQUENCE: 2
ggtaccgggc cccccctcga ggtcgacggt atcgataccg tcgacctcga ggggggggccc    60 ggtacc                                                               66

<210> SEQ ID NO 3
<211> LENGTH: 10
<212> TYPE: RNA
<213> ORGANISM: Artificial Sequence
<220> FEATURE:
<223> OTHER INFORMATION: Example mRNA poly (A) tail

<400> SEQUENCE: 3
aaaaaaaaaa                                                           10

<210> SEQ ID NO 4
<211> LENGTH: 456
<212> TYPE: DNA
<213> ORGANISM: Nicotiana tabacum

<400> SEQUENCE: 4
ggcacgaggc tcccattaat atttcttctt ctgtgtaatt ccattattct gtagtagatt    60
cacgtccgag tttaaagaag agagaaaact gaaaaggcag aaaattccag agctttagat   120
ttagccaaag atagttatgg tcgtgttgtt cttggtgaag attggcaaag taggagccaa   180
tggaagaaac taagatcata atcaatcgcc caaaaacaa ccttgttcat tctatggttt    240
ttctcttcgg tttctatgtt tgggattggg aattcctcac tgtcctttttg cttttcagtt  300 attgctcctt ctaattttcc ctagctagga tcttctcaat taatttcctt tttcattttc   360
aactaactca taattagccc aaatcttcaa aagagttttg tgtaagttga tagacgttta   420
gagaaacaga gaaatacagg ggaaaaacaa gggatg                             456

<210> SEQ ID NO 5
<211> LENGTH: 35
<212> TYPE: DNA
<213> ORGANISM: Artificial Sequence
<220> FEATURE:
<223> OTHER INFORMATION: PCR primer

<400> SEQUENCE: 5
aagtaagctt ggcacgaggc tcccattaat atttc                               35

<210> SEQ ID NO 6
<211> LENGTH: 34
<212> TYPE: DNA
<213> ORGANISM: Artificial Sequence
<220> FEATURE:
<223> OTHER INFORMATION: PCR primer

<400> SEQUENCE: 6
ggaccatggc ttgttttttcc cctgtatttc tctg                               34
```

<210> SEQ ID NO 7
<211> LENGTH: 36
<212> TYPE: RNA
<213> ORGANISM: Artificial Sequence
<220> FEATURE:
<223> OTHER INFORMATION: Artificial spacer

<400> SEQUENCE: 7
gcgugggcgg cgugggcguu uguucuuugu uugacc                               36

<210> SEQ ID NO 8
<211> LENGTH: 506
<212> TYPE: DNA
<213> ORGANISM: Homo sapiens

<400> SEQUENCE: 8
ccttctcccc ggcggttagt gctgagagtg cggagtgtgt gctccgggct cggaacacac     60
atttattatt aaaaaatcca aaaaaatct aaaaaatct tttaaaaaac cccaaaaaaa     120
tttacaaaaa atccgcgtct cccccgccgg agacttttat ttttttttctt cctcttttat    180 aaaataaccc ggtgaagcag ccgagaccga cccgccccgcc cgcggccccg cagcagctcc    240
aagaaggaac caagagaccg aggccttccc gctgcccgga cccgacaccg ccaccctcgc    300
tccccgccgg cagccggcag ccagcggcag tggatcgacc ccgttctgcg gccgttgagt    360
agttttcaat tccggttgat ttttgtccct ctgcgcttgc tccccgctcc cctcccccg     420 gctccggccc ccagccccgg cactcgctct cctcctctca cggaaaggtc gcggcctgtg    480
gccctgcggg cagccgtgcc gagatg                                         506

<210> SEQ ID NO 9
<211> LENGTH: 139
<212> TYPE: DNA
<213> ORGANISM: Homo sapiens

<400> SEQUENCE: 9
gacggggtgg gggtgggggg gaccccggtt gtgcagtttg atattgaggg agccccccacc   60 tactcgctgg ggctgcgtaa tctgtacgct tccaaactga agcgaaggcg tcgggagact    120
baggcctcag agaaccatg                                                 139

<210> SEQ ID NO 10
<211> LENGTH: 178
<212> TYPE: DNA
<213> ORGANISM: Homo sapiens

<400> SEQUENCE: 10
gcattccgtg ctatgattca ggcctaatta agtgattgcg tctgggcacg gctataaacc    60
actagctgct tcaactggta atccagtcag taggcaactg caggggctcg ccactgactg    120
aaggcagtgg aaggttggca gaaggaggct gttcaaggct gttttttgcct tcactatg      178

<210> SEQ ID NO 11
<211> LENGTH: 151
<212> TYPE: DNA
<213> ORGANISM: Homo sapiens

<400> SEQUENCE: 11
ttaagtgatt gcgtctgggc acggctataa accactagct gcttcaactg gtaatccagt    60
cagtaggcaa ctgcaggggc tcgccactga ctgaaggcag tggaaggttg gcagaaggag    120
gctgttcaag gctgttttg ccttcactat g                                    151

<210> SEQ ID NO 12
<211> LENGTH: 273
<212> TYPE: DNA
<213> ORGANISM: Homo sapiens

<400> SEQUENCE: 12

```
gggaaacagg caattaaaga gggtggagca ggtggcggtt ttggctcccc catggacatc      60
tttgatatgt tttttggagg aggaggaagg atgcagagag aaaggagagg taaaaatgtt     120
gtacatcagc tctcagtaac cctagaagac ttatataatg gtgcaacaag aaaactggct     180
ctgcaaaaga atgtgatttg tgacaaatgt gaaggtagag gaggtaagaa aggagcagta     240
gagtgctgtc ccaattgccg aggtactgga atg                                  273
```

<210> SEQ ID NO 13
<211> LENGTH: 776
<212> TYPE: DNA
<213> ORGANISM: Homo sapiens

<400> SEQUENCE: 13

```
gccagcgcag gggcttctgc tgagggggca ggcggagctt gaggaaaccg cagataagtt      60
tttttctctt tgaaagatag agattaatac aactacttaa aaaatatagt caataggtta     120
ctaagatatt gcttagcgtt aagttttta cgtaattta atagcttaag attttaagag     180
aaaatatgaa gacttagaag agtagcatga ggaaggaaaa gataaaaggt ttctaaaaca     240
tgacggaggt tgagatgaag cttcttcatg gagtaaaaaa tgtatttaaa agaaaattga     300
gagaaaggac tacagagccc cgaattaata ccaatagaag ggcaatgctt ttagattaaa     360
atgaaggtga cttaaacagc ttaaagttta gtttaaaagt tgtaggtgat taaaataatt     420
tgaaggcgat cttttaaaaa gagattaaac cgaaggtgat taaaagacct tgaaatccat     480
gacgcaggga gaattgcgtc atttaaagcc tagttaacgc atttactaaa cgcagacgaa     540
aatggaaaga ttaattggga gtggtaggat gaaacaattt ggagaagata gaagtttgaa     600
gtggaaaact ggaagacaga agtacggaaa ggcgaagaaa agaatagaga agataggaa     660
attagaagac tttagtgtca gtcaccaaag aaggcctgga acttccagag gatgaagaag     720
agaaaaagaa gcaggaagag aaaaaaacaa agtttgagaa cctctgcaaa atcatg        776
```

<210> SEQ ID NO 14
<211> LENGTH: 714
<212> TYPE: DNA
<213> ORGANISM: Homo sapiens

<400> SEQUENCE: 14

```
gcgtgaagag ctgcagtgtc actcttaaag ctgaattaat ctctgccatt ccttaaggaa      60
acaggcaact gtcttaaaac cgtggtttgg aaaatatttt gttcaagata aaactgtttt     120
aagatatatg tatatatatc ttatatatct gtattcgcat ggtaacatat cttcggtctt     180
cctgccgctg ggctctcagc ggccctccaa ggcagcccgc aggcccgtgc tcgcctcagg     240
gatcctccac agccccgggg agaccttgcc tctaaagttg ctgcttttgc agctctgcca     300
caaccgcgcg tcctcagagc cagccgggag gagctagaac cttccccgcg tttctttcag     360
cagccctgag tcagaggcgg gctggccttg caagtagccg cccagccttc ttcggtctca     420
cggaccgatc cgcccgaacc ttctcccggg gtcagcgccg cgctgcgccg cccggctgac     480
tcagcccggg cggcggggcg ggaggctctc gactgggcgg gaaggtgcgg gaaggttcgc     540
ggcggcgggg tcggggaggt gcaaaaggat gaaaagcccg tggacggagc tgagcagatc     600
```

| | |
|---|---|
| cggccgggct ggcggcagag aaaccgcagg gagagcctca ctgctgagcg cccctcgacg | 660 |
| cgggcggcag cagcctccgt ggcctccagc atccgacaag aagcttcagc catg | 714 |

<210> SEQ ID NO 15
<211> LENGTH: 344
<212> TYPE: DNA
<213> ORGANISM: Homo sapiens

<400> SEQUENCE: 15

| | |
|---|---|
| aattaattt gattacattt aaaattctat atggcaaaaa taccataatt aaagataaaa | 60 |
| ggcaaagaac aaattgggaa aaatatttt caacatatat aaccaagggc taatttctct | 120 |
| aacacctaaa aagttcttat aaatcaataa aaagaaaacc aacatctcaa tggaaaaga | 180 |
| acaaagctca taaagagttc atagaaaaag gatatacaaa tggctttaaa catgtgaaag | 240 |
| aatgttcaac ttcactcaca ataagaaaaa atacaaatta tgagttgctt cagcatcctg | 300 |
| gtgttgctgt gccgtgggtc ctgtgcggtc acttagccaa gatg | 344 |

<210> SEQ ID NO 16
<211> LENGTH: 131
<212> TYPE: DNA
<213> ORGANISM: Nicotiana tabacum

<400> SEQUENCE: 16

| | |
|---|---|
| cacaattcca catattcatt gacatactac ggcccttctt ccctaattt aagacaaagg | 60 |
| aaaaaaagta attattgatt cttctaggat ttacaatttt tgttgacgaa ttttccaaaa | 120 |
| aaaaaaatat g | 131 |

<210> SEQ ID NO 17
<211> LENGTH: 125
<212> TYPE: DNA
<213> ORGANISM: Nicotiana tabacum

<400> SEQUENCE: 17

| | |
|---|---|
| ggcacgaggc aatttcagtt gtgatctttc atgatttcca taaaagagtg agctttagca | 60 |
| agaatacaga aaccccagt tgccaagaag caattttac tgtggttttt caagatttag | 120 |
| ctatg | 125 |

<210> SEQ ID NO 18
<211> LENGTH: 51
<212> TYPE: DNA
<213> ORGANISM: Nicotiana tabacum

<400> SEQUENCE: 18

| | |
|---|---|
| aaaaaaaaa aaaaaaaaa aaaaaaaaa aaagaaaaa agaaaaaat g | 51 |

<210> SEQ ID NO 19
<211> LENGTH: 83
<212> TYPE: DNA
<213> ORGANISM: Oryza sativa

<400> SEQUENCE: 19

| | |
|---|---|
| gtgagagtga acaagagata agctaagcta gtacagcaac cagcaagaac aaagaagagt | 60 |
| ggccggagtg ggcgggggag atg | 83 |

<210> SEQ ID NO 20
<211> LENGTH: 123
<212> TYPE: DNA
<213> ORGANISM: Nicotiana tabacum

```
-continued

<400> SEQUENCE: 20
cgttgctgtc ggagattttg tatctgcgaa taaaaagagg agagggaagt aaacaaaaaa      60
atcggaaaaa gtttgaaaaa gaaaattatc tttattattt tttttttgtg ttgatttgag     120
atg                                                                   123

<210> SEQ ID NO 21
<211> LENGTH: 53
<212> TYPE: DNA
<213> ORGANISM: Cuscuta japonica

<400> SEQUENCE: 21
gaaattgaaa ggattattgc ataagaaaag ctaagatcgt cacttcaaaa atg             53

<210> SEQ ID NO 22
<211> LENGTH: 117
<212> TYPE: DNA
<213> ORGANISM: Triticum aestivum

<400> SEQUENCE: 22
tcgaaatcag agaggggcaa agcaaatcgc accaggcaaa ctcagagggt cttccggcga      60
accccaaagc gagagagcga gcgagcgatt cccaggagag gagaggaggc ggagatg        117

<210> SEQ ID NO 23
<211> LENGTH: 81
<212> TYPE: DNA
<213> ORGANISM: Zea mays

<400> SEQUENCE: 23
ccacaacagc gaaggagaaa gcagaccaac ctagccaccc agggagaaag aggccaaaag      60
ggaggggaga gtgtcgtcat g                                                81

<210> SEQ ID NO 24
<211> LENGTH: 248
<212> TYPE: DNA
<213> ORGANISM: Triticum aestivum

<400> SEQUENCE: 24
ggatccccca attctggttt ttgacctggg gaggaggcac ctttgatgtt tcagttctcg      60
aagttggtga tggtgttttt gaggtgctgt ctacatctgg tgatactcac ccttggtggt     120
gatgactttg acaagagaat tgttgattgg ctggctggaa gcttcaagaa tgatgagggt     180
attgacctgc taaaagacaa gcaagctctc cagactgtct tacagaagca gctgagaagg     240
ccaagatg                                                              248

<210> SEQ ID NO 25
<211> LENGTH: 240
<212> TYPE: DNA
<213> ORGANISM: Funaria hygrometrica

<400> SEQUENCE: 25
gatcggattg agtgatacga cttgtggagt gttggttcgt ggcatgcgcg ttgtcgaaag      60
agtggttgca ggcgatatcg cagtggggac tcgggttttt tcaattctct cgtggagttc     120
gttcgtccag ctgatcgctc ccgacgcttg tgggttgtag ctcgggtggc attgcggtcg     180
aggttggtga gggtgatcgc tgggtggagc gcattgtcga ggagcggaga ggtaggcatg     240

<210> SEQ ID NO 26
<211> LENGTH: 147
<212> TYPE: DNA
```

<213> ORGANISM: Zea mays

<400> SEQUENCE: 26

```
ggcacgagag aaaaactagc cgaagcaaac ccattccaca agcacctggt gggatcatct      60
catcatcaga aacaaagaga gagattccgt gcccacttgt tgtagtagat tgtgaggatt     120
gaggagtagc aaagagaagc agccatg                                         147
```

<210> SEQ ID NO 27
<211> LENGTH: 147
<212> TYPE: DNA
<213> ORGANISM: Triticum aestivum

<400> SEQUENCE: 27

```
ggcacgagag aaaaactagc cgaagcaaac ccattccaca agcacctggt gggatcatct      60
catcatcaga aacaaagaga gagattccgt gcccacttgt tgtagtagat tgtgaggatt     120
gaggagtagc aaagagaagc agccatg                                         147
```

<210> SEQ ID NO 28
<211> LENGTH: 45
<212> TYPE: DNA
<213> ORGANISM: Arabidopsis thaliana

<400> SEQUENCE: 28

```
tttaaccagt tcataagaaa gaggaaagat aagtaattaa taatg                      45
```

<210> SEQ ID NO 29
<211> LENGTH: 35
<212> TYPE: DNA
<213> ORGANISM: Artificial Sequence
<220> FEATURE:
<223> OTHER INFORMATION: PCR primer

<400> SEQUENCE: 29

```
gcggcaagct tcgttgctgt cggagatttt gtatc                                 35
```

<210> SEQ ID NO 30
<211> LENGTH: 49
<212> TYPE: DNA
<213> ORGANISM: Artificial Sequence
<220> FEATURE:
<223> OTHER INFORMATION: PCR primer

<400> SEQUENCE: 30

```
cgcgccatgg caaatcaaca caaaaaaaa caaaaaaaaa ataataaag                    49
```

<210> SEQ ID NO 31
<211> LENGTH: 32
<212> TYPE: DNA
<213> ORGANISM: Artificial Sequence
<220> FEATURE:
<223> OTHER INFORMATION: PCR primer

<400> SEQUENCE: 31

```
gcggcaagct tcacaattcc acatattcat tg                                    32
```

<210> SEQ ID NO 32
<211> LENGTH: 33
<212> TYPE: DNA
<213> ORGANISM: Artificial Sequence
<220> FEATURE:
<223> OTHER INFORMATION: PCR primer

<400> SEQUENCE: 32
```

-continued

```
cgcgccatgg ttttttttttt tggaaaattc gtc                                   33
```

<210> SEQ ID NO 33
<211> LENGTH: 884
<212> TYPE: DNA
<213> ORGANISM: Encephalomyocarditis virus

<400> SEQUENCE: 33

```
ttgaaagccg ggggtgggag atccggattg ccagtctact cgatatcgca ggctgggtcc       60
gtgactaccc actcctactt tcaacgtgaa ggctacgata gtgccagggc gggtactgcc      120
gtaagtgcca ccccaaccaa caaaacaaaa accccccccc cccccccccc cccccccccc      180
cccccccccc cccccccccc cccccccccc cccccccccc cccccccccc cccccccccc      240
cccccccccc cccccccccc ccccccccca acgttactgg ccgaagccgc ttggaataag      300
gccggtgtgc gtttgtctat atgttatttc taccacatca ccgtcttttg gtggtgtgag      360
ggcccggaac ctggccctgt cttcttgacg agcattccta ggggtctttc ccctctcgcc      420
aaaggaatgt aaggtctgtt gaatgtcgtg aaggaagcag ttcctctgga agcttcttga      480
agacaagcaa cgtctgtagc gacccttttgc aggcagcgga aatccccacc tggtaacagg      540
tgcctctgcg gccaaaagcc acgtgtataa gatacacctg caaaggcggc acaaccccag      600
tgccacgttg tgagttggat agttgtgaa agagtcaaat ggctcacctc aagcgtattc       660
aacaagggc tgaaggatgc ccagaaggta ccccattgta tgggatctga tctggggcct      720
cggtgcacgt gctctacacg tgttgagtcg aggttaaaaa acgtctaggc ccccgaacc       780
acgggggacgt ggttttcctt tgaaaaccac gattgtaaga tggctacaac tatggaacaa      840
gagatttgtg cgcattccct cacgtttaaa ggatgcccga aatg                       884
```

<210> SEQ ID NO 34
<211> LENGTH: 745
<212> TYPE: DNA
<213> ORGANISM: Poliovirus

<400> SEQUENCE: 34

```
ttaaaacagc tctggggttg ttcccacccc agaggcccac gtggcggcta gtacactggt       60
atcacggtac ctttgtacgc ctgttttata ctccctcccc cgcaacttag aagcatacaa      120
ttcaagctca ataggagggg gtgcaagcca gcgcctccgt gggcaagcac tactgttttcc     180
ccggtgaggc cgcatagact gttcccacgg ttgaaagtgg ccgatccgtt atccgctcat      240
gtacttcgag aagcctagta tcgctctgga atcttgacg cgttgcgctc agcactcaac       300
cccggagtgt agcttgggcc gatgagtctg gacagtcccc actggcgaca gtggtccagg      360
ctgcgctggc ggcccacctg tggcccaaag ccacggacg ctagttgtga acagggtgtg       420
aagagcctat tgagctacat gagagtcctc cggcccctga atgcggctaa tcctaaccat      480
ggagcaggca gctgcaaccc agcagccagc ctgtcgtaac gcgcaagtcc gtggcggaac      540
cgactacttt gggtgtccgt gtttccttttt attcttgaat ggctgcttat ggtgacaatc     600
atagattgtt atcataaagc gagttggatt ggccatccag tgtgaatcag attaattact      660
cccttgtttg ttggatccac tcccgaaacg ttttactcct taacttattg aaattgtttg      720
aagacaggat ttcagtgtca caatg                                            745
```

<210> SEQ ID NO 35
<211> LENGTH: 403
<212> TYPE: DNA
<213> ORGANISM: Hepatitis C virus

<400> SEQUENCE: 35

```
ggtcatcttg gtagccacta taggtgggtc ttaagggttg gtcaaggtcc ctctggcgct    60
tgtggcgaga aagcgcacgg tccacaggtg ttggccctac cggtgtgaat aagggcccga   120
cgtcaggctc gtcgttaaac cgagcccatt acccacctgg gcaaacaacg cccacgtacg   180
gtccacgtcg ccctacaatg tctctcttga ccaataggct ttgccggcga gttgacaagg   240
accagtgggg gctgggcggc gggggaagga cctccgtcgc tgcccttccc ggtgggtgg    300
gaaatgcatg gggccaccca gctccgcggc ggcctgcagc cggggtagcc caaaaacctt   360
cggggtgaggg cgggtggcat ttttctttcc tataccgatc atg                    403
```

<210> SEQ ID NO 36
<211> LENGTH: 56
<212> TYPE: RNA
<213> ORGANISM: Plautia stali inetstine virus

<400> SEQUENCE: 36

```
acccucgugc ucgcucaaac auuaaguggu guugugcgaa aagaaucuca cuucaa        56
```

<210> SEQ ID NO 37
<211> LENGTH: 580
<212> TYPE: DNA
<213> ORGANISM: Homo sapiens

<400> SEQUENCE: 37

```
aagaagaggt agcgagtgga cgtgactgct ctatcccggg caaaagggat agaaccagag    60
gtggggagtc tgggcagtcg gcgacccgcg aagacttgag gtgccgcagc ggcatccgga   120
gtagcgccgg gctccctccg gggtgcagcc gccgtcgggg gaagggcgcc acaggccggg   180
aagacctcct cccttttgtgt ccagtagtgg ggtccaccgg agggcggccc gtgggccggg   240
cctcaccgcg gcgctccggg actgtggggt caggctgcgt tgggtggacg cccacctcgc   300
caaccttcgg aggtccctgg gggtcttcgt gcgcccgggg gctgcagaga tccaggggag   360
gcgcctgtga ggcccggacc tgccccgggg cgaagggtat gtggcgagac agagccctgc   420
acccctaatt cccggtggaa aactcctgtt gccgtttccc tccaccggcc tggagtctcc   480
cagtcttgtc ccggcagtgc cgccctcccc actaagacct aggcgcaaag gcttggctca   540
tggttgacag ctcagagaga gaaagatctg agggaagatg                         580
```

<210> SEQ ID NO 38
<211> LENGTH: 861
<212> TYPE: DNA
<213> ORGANISM: Homo sapiens

<400> SEQUENCE: 38

```
ctgctcgcgg ccgccaccgc cgggccccgg ccgtccctgg ctcccctcct gcctcgagaa    60
gggcagggct tctcagaggc ttggcgggaa aaagaacgg agggagggat cgcgctgagt   120
ataaaagccg gttttcgggg ctttatctaa ctcgctgtag taattccagc gagaggcaga   180
gggagcgagc gggcggccgg ctaggtggga agagccgggc gagcagagct cgcctgcggg   240
cgtcctggga agggagatcc ggagcgaata gggggcttcg cctctggccc agccctcccg   300
cttgatcccc caggccagcg gtccgcaacc cttgccgcat ccacgaaact ttgcccatag   360
cagcgggcgg gcactttgca ctggaactta caacacccga gcaaggacgc gactctcccg   420
acgcggggag gctattctgc ccatttgggg acacttcccc gccgctgcca ggacccgctt   480
ctctgaaagg ctctccttgc agctgcttag acgctggatt ttttttcgggt agtggaaaac   540
```

-continued

| | |
|---|---|
| cagcagcctc ccgcgacgat gcccctcaac gttagcttca ccaacaggaa ctatgacctc | 600 |
| gactacgact cggtgcagcc gtatttctac tgcgacgagg aggagaactt ctaccagcag | 660 |
| cagcagcaga gcgagctgca gccccggcg cccagcgagg atatctggaa gaaattcgag | 720 |
| ctgctgccca ccccgcccct gtcccctagc cgccgctccg gctctgctc gccctcctac | 780 |
| gttgcggtca caccctctc ccttcgggga gacaacgacg gcggtggcgg gagcttctcc | 840 |
| acggccgacc agctggagat g | 861 |

<210> SEQ ID NO 39
<211> LENGTH: 225
<212> TYPE: DNA
<213> ORGANISM: Homo sapiens

<400> SEQUENCE: 39

| | |
|---|---|
| aggtcgacgc cggccaagac agcacagaca gattgaccta ttggggtgtt tcgcgagtgt | 60 |
| gagagggaag cgccgcggcc tgtatttcta gacctgccct tcgcctggtt cgtggcgcct | 120 |
| tgtgaccccg ggcccctgcc gcctgcaagt cggaaattgc gctgtgctcc tgtgctacgg | 180 |
| cctgtggctg gactgcctgc tgctgcccaa ctggctggca agatg | 225 |

<210> SEQ ID NO 40
<211> LENGTH: 259
<212> TYPE: DNA
<213> ORGANISM: Homo sapiens

<400> SEQUENCE: 40

| | |
|---|---|
| caatcccaca gagtattgat gaggaaactg aagtttggag cgatcacatc attttcccaa | 60 |
| ggtaacacaa gtggcaagac agccgggaac ccctacccca tcccttatt cagcacatga | 120 |
| aataaacaag gggcatccaa atcttgcggc aacgcccccg ggacatgcat cgtcccctgg | 180 |
| actctctcaa acccttatc cctctggaca gaatgcaggt ccaaccacgc tggtataccc | 240 |
| tcaaacccct cagacaatg | 259 |

<210> SEQ ID NO 41
<211> LENGTH: 252
<212> TYPE: DNA
<213> ORGANISM: Rattus norvegicus

<400> SEQUENCE: 41

| | |
|---|---|
| gcgggggcgc gcggggccgg ggtgcaggcg gggacgcggg ggtgacgcgg gcccgggccg | 60 |
| ctgtagcaca caggggctcg gtctctcggc ttcaggcgga gtccggctgc actaggctgg | 120 |
| gagcgcggcg ggacgcgaac cgggaggctg gcagcccgcg ggcgagccgc gctgggggc | 180 |
| cgaggccggg gtcggggccg gggagccccg agagctgccg cagcggggtc ccggggccgc | 240 |
| ggagggggcca tg | 252 |

<210> SEQ ID NO 42
<211> LENGTH: 206
<212> TYPE: DNA
<213> ORGANISM: Homo sapiens

<400> SEQUENCE: 42

| | |
|---|---|
| ggcactggct gggagggcgc cctgcaaagt tgggaacgcg gagccccgga cccgctcccg | 60 |
| ccgcctccgg ctcgcccagg gggggtcgcc gggaggagcc cggggagag ggaccaggag | 120 |
| gggcccgcgg cctcgcaggg gcgccccgcg ccccaccct gccccgcca gcggaccggt | 180 |
| ccccacccc cggtccttcc accatg | 206 |

<210> SEQ ID NO 43
<211> LENGTH: 332
<212> TYPE: DNA
<213> ORGANISM: Rattus norvegicus

<400> SEQUENCE: 43

```
gtcaggctct ggcttggagc tggggaggcg gggtgggggg gtggggggggg tcgggctgca      60 taatgaggac tgggggtttt ttggatgccc ccttccggct ccgcgagacg gcggaccttg     120
gcggtccccc gagcgagcgc gacgctaatc gagggctgct cggctcgaga ggccggggcc     180
cgccgcccag cagagttgtg tttttcctga tcggggctcg ggccgcccct cctccgggac     240
cctcccctcg ggaaccgtcg cccgcggcgg ttagttagga ctggattgct tggcgcgaaa     300
aggtggacaa gtcgtatttt caagagaaga tg                                   332
```

<210> SEQ ID NO 44
<211> LENGTH: 51
<212> TYPE: RNA
<213> ORGANISM: Homo sapiens

<400> SEQUENCE: 44

```
cccgagccgg cgggugcggg cgguggcagc ggggcccgga ugggcgcccg g               51
```

IDENTIFICATION OF EUKARYOTIC INTERNAL RIBOSOME ENTRY SITE (IRES) ELEMENTS

CROSS-REFERENCE TO RELATED APPLICATIONS

The present application is a 35 U.S.C. §371 National Phase Application of International Application Serial No. PCT/EP02/09844, filed Sep. 3, 2002 and published in English as PCT Publication No. WO 03/020928 on Mar. 13, 2003, which claims priority to German Patent Application Serial No. DE 101 43 238.0, filed Sep. 4, 2001, the disclosures of each of which are incorporated herein by reference in their entireties.

FIELD OF INVENTION

The present invention is directed to a method of search and identification novel eukaryotic IRES elements active in plant, mammalian and yeast cells and to a process of expressing a nucleotide sequence of interest in eukaryotic cells cap-independently using an IRES element identified or identifyable according to the above method. The invention further relates to IRES elements identified or identifyable according to the above method and to transgenic or transiently transfected eukaryotic cells transformed with a vector containing such an IRES element.

BACKGROUND OF THE INVENTION

There is a growing interest in using internal ribosome entry site (IRES) elements for cap-independent expression of foreign genes in eukaryotic cells. Although the number of published nucleotide sequences shown to promote cap-independent translation is increasing rapidly, identification of new IRESes published so far was occasional and accidental and there is no distinct methodology of prediction of IRES activity.

Translation initiation of mRNAs in eukaryotic cells is a complex process that involves the concerted interaction of numerous factors (Pain (1996) Eur. J. Biochem. 236, 747-771). For most mRNAs, the first step is the recruitment of ribosomal 40S subunits onto the mRNA at or near the capped 5' end (FIG. 1). Association of 40S to mRNA is greatly facilitated by the cap-binding protein complex eIF4F. Factor eIF4F is composed of three subunits: the RNA helicase eIF4A, the cap-binding protein eIF4E, and the multi-adaptor protein eIF4G which acts as a scaffold for the proteins in the complex and has binding sites for eIF4E, eIF4a, eIF3, and poly(A) binding protein.

Infection of cells by a variety of RNA viruses results in the selective inhibition of translation of host but not of viral mRNAs. For example, infection of cells with poliovirus, a cytoplasmic RNA virus, results in the modification of several translation initiation factors. Specifically, the proteolysis of both forms of eIF4G, eIF4GI and eIF4GII (Gradi et al., (1998) Proc. Natl. Acad. Sci. USA 95, 11089-11094) by virally encoded proteases results in inhibition of translation of most capped cellular mRNAs. In contrast, the translation of polioviral mRNA, which contains a 450-nt sequence in the viral 5' noncoding region (5'NCR) that can recruit 40S subunits in the absence of intact eIF4F, is not inhibited. This sequence element was termed an <<internal ribosome entry site>> or <<IRES>> (Jang et al., 1988. J. Virol. 62, 2363-2643). Such IRES elements have been found in picornaviral, flaviviral, pestiviral, retroviral, lentiviral and insect viral RNAs (Table 1) and animal cellular RNAs (Table 2). IRES containing animal mRNAs can presumably recruit 40S ribosomes both via either their capped 5' ends or their IRES elements that is likely to make possible the translation under conditions where cap-dependent translation is reduced, for example, during viral infection, at the G2/M phase of cell cycle, and under conditions of stress and apoptosis (Johannes et al., (1999) Proc. Natl. Acad. Sci. USA 96, 13118-13123; Cornelis et al., (2000) Molecular Cell 5, 597-605; Pyronnet et al., (2000) Molecular Cell 5, 607-616; Stein et al., 1998. Mol. and Cell. Biol. 18, 3112-3119; Holcik et al., 2000. Oncogene 19, 4174-4177; Stoneley et al., 2000. Mol. and Cell. Biol. 20, 1162-1169). Up to 3% of cellular mRNAs of animal are translated at reduced concentrations of cap binding complex eIF4F (Johannes et al., (1999) Proc. Natl. Acad. Sci. USA 96, 13118-13123).

Over the past few years a reconstituted ribosome binding assay has allowed for the elucidation of the mechanisms by which various IRES elements work (Pestova et al., 1998. Genes Dev. 12, 67-83). Some of these elements act by providing a high-affinity binding site for the RNA binding surface on eIF4G. Others work by binding to eIF3 and/or the 40S subunit (see FIG. 2). Recently, an important role of direct IRES RNA/18S rRNA interaction has been shown. The Gtx IRES contains several nonoverlapping segments having complementarity to 18S rRNA that were shown to mediate internal initiation of translation (Hu et al., 1999. Proc. Natl. Acad. Sci. USA 96, 1339-1344). Within one of these segments, a 9-nt GC-rich sequence CCGGCGGGU which is 100% complementary to 18S rRNA at nucleotides 1132-1124 was identified. It was shown that synthetic IRESes composed of multiple linked copies of this 9-nt IRES module increased internal initiation dramatically in animal cells (Chappel et al., 2000. Proc. Natl. Acad. Sci. USA 97, 1536-1541).

5' leaders of several plant viral polycistronic genomic RNAs, including members of the potyviral, comoviral families, are responsible for conferring cap-independent translation. Tobamoviruses and potexvirus X IRESes are located in internal parts of the viral genome (Table 2). Tobacco mosaic tobamovirus (TMV) is a positive-stranded RNA plant virus with a monopartite genome 6395 nucleotides (nt) in length (Goelet et al., 1982. Proc. Natl. Acad. Sci. USA 79, 5818-5822). The 5' proximal ORFs encoding replicative proteins are expressed directly from the genomic RNA, with the smaller (126 kDa) protein produced approximately >10 times the level of the 183 kDa protein which is produced by occasional readthrough of the stop codon for the 126-kDa ORF (Pelham, 1978, Nature 272, 469-471). Although some replication can occur with only the larger protein, both proteins are required for efficient replication (Ishikawa et al., 1986. Nucl. Acid. Res. 14, 8291-8305). The remaining TMV gene products, the movement protein (MP) and the coat protein (CP), are expressed from 3' coterminal subgenomic mRNAs (sgRNAs) (reviewed by Palukaitis and Zaitlin, 1986 In: "The plant virus". M. H. V. van Regenmortel and M. Fraenkel-Conrat, Eds. Vol. 2, pp. 105-131. Plenum Press, NY). Thus, the internal movement protein (MP) gene and the 3'-proximal coat protein gene cannot be translated from genomic RNA of typical tobamoviruses (TMV UI is the type member of the genus *Tobamovirus*). The dicistronic intermediate-length RNA-2 called sgRNA $I_2$ RNA is translated to produce the 30-kDa MP (Bruening et al., 1976 Virology 71, 498-517; Higgins et al., 1976 Virology 71, 486-497; Beachy and Zaitlin, 1977 Virology 81, 160-169; Goelet and Karn, 1982 J. Mol. Biol. 154, 541-550), whereas the 3'-proximal coat protein (CP) gene of $I_2$ RNA is translationally silent. This gene is expressed only from small monocistronic sgRNA (Siegel et al., 1976 Virology 73, 363-371; Beachy and Zaitlin, 1977 Virology 81, 160-169).

It has been shown (Ivanov et al., 1997, Virology 232, 32-43) that, unlike RNA of typical tobamoviruses, the translation of the CP gene of a crucifer-infecting tobamovirus (crTMV) occurred in vitro by an internal ribosome entry mechanism. The genome of crTMV (6312 nts) contains four traditional genes encoding two components of the replicase (the proteins of 122-kDa and 178-kDa, the readthrough product of 122-kDa), 30-kDa MP and 17-kDa CP (Dorokhov et al., 1993 Dokl. Russian Acad Sci. 332, 518-52; Dorokhov et al., 1994 FEBS Lett. 350, 5-8). It was found that the 148-nt region upstream of the CP gene of crTMV RNA contained an internal ribosome entry site ($IRES_{CP148}$), promoting internal translation initiation of the CP gene and of different reporter genes (Ivanov et al., (1997) Virology 232, 32-43). By analogy with crTMV, the 3'-proximal CP gene of potato virus X occurs by a mechanism of internal initiation (Hefferon et al., 1997 J. Gen. Virol. 78, 3051-3059; Hefferon et al., 2000. Arch. Virol. 145, 945-956). The capacity of crTMV IRE-$S^{CR}_{CP}$ for mediating internal translation distinguishes this tobamovirus from well-known type member of the genus, TMV U1. The equivalent 148-nt sequence from TMV U1 RNA was incapable ($UI_{CP,148}^{SP}$) of mediating internal translation (Ivanov et al., (1997) Virology 232, 32-43).

Recently, it has been shown that the 228- and 75-nt regions upstream of the MP gene of crTMV and TMV U1 RNAs contained IRES elements, $IRES_{MP,75}^{CR}$ or $IRES_{MP,228}^{CR}$, which directed expression of the 3'-proximal reporter genes from dicistronic constructs in cell-free translation systems and in isolated protoplasts (Skulachev et al., 1999, Virology 263, 139-154). Moreover, the equivalent sequence from TMV U1 RNA used as the intercistronic spacer ($IRES_{MP,75}^{U1}$) was able to mediate internal translation of the second gene in dicistronic transcripts.

There are several inventions wherein an IRES element was used for cap-independent expression of foreign gene(s) in linear multicistronic mRNAs via IRES elements in mammalian cells (U.S. Pat. No. 6,060,273; U.S. Pat. No. 6,114,146; U.S. Pat. No. 5,358,856; U.S. Pat. No. 6,096,505; U.S. Pat. No. 171,821; U.S. Pat. No. 5,766,903), plant cells (WO98/54342) and generally, in eukaryotic cells (U.S. Pat. No. 171, 821; U.S. Pat. No. 5,766,903; U.S. Pat. No. 5,925,565; U.S. Pat. No. 6,114,146). To provide cap-independent IRES-mediated expression of a gene, a circular RNA was developed as well (U.S. Pat. No. 5,766,903). Cap-independent translation of eukaryotic mRNA could be reached by using 5'UTR of barley yellow dwarf virus RNA that is principally different from known IRESes (U.S. Pat. No. 5,910,628). Generally, all inventions used natural IRESes isolated from animal (e.g. U.S. Pat. No. 5,358,856) or plant viruses (WO98/54342) not having cross-kingdom activity, i.e. these IRESes are limited to either plant or animal cells. There are no inventions developing approaches for the creation of non-natural, artificial IRESes that are capable to provide efficient cap-independent gene expression in animal and plant cells. Moreover, there are no approaches for searching new IRES elements having cross-kingdom activity.

In contrast to animal cell mRNA, there are no published reports on IRES-mediated mRNA translation initiation in plant cells (see Table 2), except for one recent patent application (WO01/59138) describing a plant IRES element of the Arabidopsis RPS18C gene. However, neither the methodology used in this patent application nor the experimental approaches nor the interpretation of the results allows a direct and unambiguous conclusion of an IRES activity in vivo, nor a reliable detection of said elements in plant transcripts. First of all, there was an incomprehensive test for IRES activity. Usually, for detecting IRES activity, the dicistronic mRNA assay is utilised (Pelletier & Sonenberg, 1988, Nature, 334, 320-325). In this test, two types of capped bicistronic mRNAs separated by a putative IRES element (with and without hairpin structure in front of the first cistron) are analysed for the ability to provide expression in vitro and in vivo. The construct without hairpin structure allows ribosome scanning and translation of the first, 5' proximal cistron, whereas cap-dependent translation of the first cistron is blocked in the construct with hairpin structure. The authors of WO01/59138 tested the putative IRES element of RPS18C only in the artificial bicistronic transcript without hairpin structure. Thus, the results presented in WO01/59138 may well be a consequence of reinitiation of translation (Kozak, 2001, Mol. Cell. Biol 21, 1899-1907). Additionally, it is known that a nucleotide sequence having IRES activity in vitro, frequently does not show IRES activity in eukaryotic cells. WO01/59138 does not contain experimental evidence showing directly and unambiguously that the putative IRES element of Arabidopsis RPS18C is functional in eukaryotic cells (plant or animal).

In contrast to animal cell mRNA, there are no published reports of in vivo cellular mRNA IRES mediated translation initiation in plant cells (Table 2). The low activity of animal virus IRESes (encephalomyocarditis virus IRES, $IRES_{EMCV}$) in plants was reported (Urwin et al., 2000 Plant J. 24, 583-589). There is no evidence of cross-kingdom (plant, animal, yeast) activity of any IRES element so far. Although the number of published nucleotide sequences that are capable to provide cap-independent translation increases constantly, identification of new IRESes happens only accidentally, and there is no distinct methodology of prediction.

It is therefore an object of the invention to provide a method for identifying novel eukaryotic IRES elements.

It is a further object of the invention to provide novel eukaryotic IRES elements, notably of plant origin.

It is a further object to provide novel IRES elements having cross-kingdom activity.

It is another object of the invention to provide a process of expressing a nucleotide sequence of interest in eukaryotic cell(s) under translational control of a novel IRES element, notably of an IRES element of plant origin.

DESCRIPTION OF THE INVENTION

The above objects are solved according to the claims of the invention.

The invention provides a method of search for and identification of a eukaryotic IRES element active in cap-independent translation of RNA in eukaryotic cells, comprising the following steps:
  (i) screening eukaryotic mRNA sequences or corresponding DNA sequences for a potential IRES element having a block of nucleotides having
    (a) a length of at least 30 nucleotides;
    (b) an adenine nucleotide content of at least 40 mol-%; and
    (c) a pyrimidine nucleotide content of less than 40 mol-%;
  (ii) inserting said potential IRES element into a linear dicistronic construct between an upstream gene and a downstream GUS reporter gene, whereby said potential IRES element is positioned for IRES-dependent translation of said downstream GUS gene and whereby said upstream gene is preceded by a stable hairpin structure to prevent IRES-independent translation of said genes; and (iii) testing said potential IRES element for IRES-dependent translation of said GUS gene in a rabbit reticulocyte lysate or in a wheat germ extract in vitro translation assay, whereby GUS gene expression is quantitated preferably relative to a construct having a reference IRES element or a non-IRES element between said upstream gene and said GUS gene.

An IRES element which gives rise to GUS expression in at least one of said in vitro translation assays may then be selected.

The inventors of the present invention have surprisingly identified criteria for identifying nucleotide sequences which exhibit IRES activity (IRES elements), i.e. sequences which are capable of providing cap-independent translation of a downstream gene or coding sequence by an internal ribosome entry mechanism. The inventors have found that nucleotide sequences having a block of at least 30 nucleotides with a high adenine content and a low pyrimidine nucleotide content have a high propensity of exhibiting IRES activity. By screening known nucleotide sequences applying the above criteria, a nucleotide sequence or a set of nucleotide sequences with a high propensity of having IRES activity can be identified. The screening of the invention constitutes a pre-selection of nucleotide sequences from all known nucleotide sequences. A pre-selected potential IRES element or a set of such potential IRES elements can then be tested experimentally for its actual (degree of) IRES activity. The screening or pre-selection according to the invention reduces the number of sequences to be tested experimentally for IRES activity enormously such that directed identification of novel IRES elements including experimental confirmation becomes possible for the first time.

Said screening may be carried out on any known nucleotide sequence and on sequences that will become known in the future. Nucleotide sequences of eukaryotic origin, i.e. plant and animal sequences are screened and those of higher plants or higher animals are more preferred. Screening of viral sequences is not within the scope of the invention.

Whole genome sequences including nuclear genomes and organelle genomes like plastid or mitochondrial genomes may be screened. Eukaryotic nuclear genome sequences are preferred. Screening may be carried out on DNA or on RNA sequences. If double-stranded DNA is used, both strands may be screened. The coding strand is screened preferentially. The screening may be restricted to 5' UTR sequences of genes. It is equivalent to screen 5' UTR sequences on the mRNA level. The screening criteria of the invention regarding adenine and pyrimidine content refer to messenger RNA or to the corresponding coding strand on the DNA level.

Screening may be carried out, in the simplest case, by eye by scanning along printed or written nucleotide sequences. This approach can be successful, especially if one focuses on 5' UTR sequences. It is more convenient to employ an automatic screening method e.g. by using a computer and a suitable computer program. In this way, large data bases of nucleotide sequences, notably genome databases, may be screened with the potential of finding many IRES elements.

Herein, "adenine-rich" or "high adenine content" means a content of adenine that is at least 40 mol-%. "Pyrimidine-poor" or "low pyrimidine content" means a content of thymine (uracil)+cytidine that is lower than 40 mol-% thymine (uracil)+cytidine. As to the criteria applied during screening, a block of at least 30 nucleotides with an adenine content of at least 40, preferably at least 50 and most preferably at least 60 mol-% is searched for. The pyrimidine content should be less than 40 mol-%, preferably less than 30 mol-%, and most preferably less than 20 mol-%.

There is no strict upper limit for the length of said block of nucleotides. For practical purposes, said block is chosen to be shorter than 500 nucleotides during screening. Said block has a length of at least 30 nucleotides. It is preferred to search for blocks between 200 and 30 nucleotides. More preferably, said block has between 40 and 100 nucleotides.

Said block of nucleotides according to the invention has a high propensity of conferring IRES activity to a sequence comprising it. When screening 5'UTR sequences, 2, 3 or even more blocks of nucleotides according to the invention may be found.

If screening is carried out with the help of a computer, it may be done multiple times, whereby the screening criteria may be changed each time. Preferably, one starts with strict criteria, i.e. high adenine content, low pyrimidine content and short nucleotide blocks in order to find sequences with the highest probability of having IRES activity. Further IRES elements may be found by applying less stringent criteria with lower adenine content, higher pyrimidine content, or longer blocks or combinations thereof, within the criteria given above. In this way, IRES elements of various IRES activities may be found, which is useful for achieving a desired expression level when a gene of interest is expressed under translational control of an IRES element.

FIG. 7 and FIG. 8 show several 5' UTR sequences containing nucleotide blocks according to the invention of human and plant origin, respectively. These 5' UTR sequences are potential IRES elements according to step (i) of claim 1. For some of these potential IRES elements cross-kingdom IRES activity is demonstrated in the examples.

A potential IRES element found in step (i) of claim 1 is then subjected to an experimental confirmation of its IRES activity. For this purpose, a test system was deviced comprising the bicistronic DNA construct "H-GFP-GUS" having the following elements in this order: a structure that forms a stable hairpin (H) on the mRNA level, a green fluorescent protein (GFP) gene (GFP coding sequence), an intercistronic spacer with restriction site(s) for inserting potential IRES elements, and the GUS gene (GUS coding sequence). A potential IRES element is inserted into the spacer between GUS and GFP. This construct is then transcribed in vitro using e.g. T7 RNA polymerase to obtain mRNA. The obtained mRNA is then translated in vitro using a rabbit reticulocyte lysate (RRL) or a wheat germ extract (WGE) in vitro translation system. Both in vitro translation systems are commercially available e.g. from Promega and from Roche Diagnostics and may be used according to the manufacturer's instructions. After translation, GUS expression may be determined e.g. via its enzymatic activity and a colorimetric detection, by autoradiography, or by Western blotting.

GUS gene expression is quantitated preferably relative to a construct having a reference IRES element or a non-IRES element between said upstream gene and said GUS gene. As a reference IRES element having strong IRES activity the nucleotide block $(GAAA)_{16}$ (SEQ ID NO:1, see examples) or any other known IRES element may be used. As a non-IRES element, said synthetic spacer referred to in FIG. 4 (see examples) may e.g. be used or a random nucleotide block.

Said hairpin structure in said bicistronic DNA construct prevents cap-dependent translation, such that all GUS expression can be ascribed to the translational activity of the potential IRES element inserted in said intercistronic spacer of said construct. Said hairpin has to be stable enough to efficiently prevent cap-dependent translation. Preferably, its stability is higher than 30 kcal/mol (see Kozak, M. (1986) Proc. Natl. Acad. Sci. USA 83, 2850-2850). Insufficient stability of said hairpin may be recognized by any expression of said GFP gene. GFP translation may be detected e.g. by way of its fluorescence, by Western blotting or by autoradiography.

The H-GFP-GUS construct used herein was built from plasmid pBluescriptII SK+, a GUS nucleotide sequence and a GFP sequence. The hairpin structure has the sequence: ggtac-cgggcccccctcgaggtcgacggtatc-gataccgtcgacctcgagggggggcccggtacc (SEQ ID NO:2). Equivalent structures can be easily created by a person skilled in the art.

All aspects in connection with these in vitro translation systems are well studied and known in the prior art. Details can be found in the following documents and in references cited therein: Anderson, C., et al. (1985) Meth. Enzymol. 101, 635; Krieg, P. and Melton, D. (1984) Nucl. Acids Res. 12, 7057; King, R. W. et al.(1997) Science 277, 973; DiDonato, J. A. and Karin, M. (1993). Promega Notes 42, 18; Pelham, H. R. B. and Jackson, R. J. (1976) Eur. J. Biochem. 67, 247; Jackson, R. J. and Hunt, T. (1983) Meth. Enzymol. 96, 50; Technical Bulletins No. 126, and No. 165 or Technical Manual No. 232, all from Promega Corp.

Potential IRES elements which give rise to GUS gene expression in such a WGE or RRL translation assay are IRES elements according to the invention. The IRES elements identified or identifyable according to the invention typically exhibit cross-kingdom activity, i.e. they can be used to express a gene of interest under translational control of said IRES in plants and in animals. In spite of said cross-kingdom activity, the activity of said IRES element is normally not the same when expression of a gene of interest is compared in plant or animal systems. Variations in expressions levels exist between the two in vitro translation systems mentioned above. In in vivo systems, these variations are in general even higher. Still, the IRES elements identified in this invention show surprisingly high IRES activity in both in vitro systems, in plant cells and in animal cells.

It should be mentioned that IRES activity may be detected not only by the above in vitro translation assays but also in plant or animal cells or in vivo. Series of synthetic sequences which were used as intercistronic spacers in the bicistronic H-GFP-GUS vectors were created and examined in RRL, tobacco protoplasts and HeLa cells. Further, we created two synthetic sequences representing four linked copies of a 19-nt direct repeat (Ecp ×4) and 16 copies of the GAAA sequence $(GAAA)_{16}$ (SEQ ID NO:1) which both turned out to function as IRES elements. The important role of adenine-rich nucleotide sequences was proven in plant and animal translation systems in vitro and in vivo.

The use of the principle of the invention allowed to reveal numerous plant eukaryotic IRES elements that are universal and are efficient translation initiation motifs for different kingdoms of living organisms. To the best of our knowledge, we have identified the first IRES elements in genomes of plant organisms.

This invention further provides a process of expressing a nucleotide sequence of interest in eukaryotic cell(s) by introducing into said cell(s) a vector comprising said nucleotide sequence of interest operably linked to an upstream IRES element identified or identifyable in accordance with the above method of search for and identification of a eukaryotic IRES element, whereby said nucleotide sequence of interest is translated cap-independently by way of said IRES element.

Said nucleotide sequence of interest may be expressed in a plant or in plant cells. It may also be expressed in an animal or in animal cells. Among animals, mammalian cells or mammalian animals including humans (e.g. for gene therapy) are preferred. Further, said nucleotide sequence of interest may be expressed in fungi, preferably in yeast cells.

The IRES element contained in said vector is of eukaryotic origin, preferably of plant or of mammalian origin. More preferably, said IRES element comprises a sequence according to one of the sequences of FIG. 7 or FIG. 8 or an IRES-functional portion thereof. Even more preferably, said IRES element is derived from the 5'UTR of one of the following plant genes: heat shock factor-1, poly(A) binding protein, 48K MAP kinase. Most preferably, these genes are from tobacco.

Said process of expressing of the invention does not comprise use of one of the sequences shown in FIG. 11 as IRES element.

Said nucleotide sequence of interest may be expressed from monocistronic mRNA. However, the high potential of IRES technology is in bicistronic or polycistronic expression, which allows to express subunits of a protein complex or engineering a whole biochemical cascade or pathway.

Said eukaryotic cells or eukaryotic organisms may be stably transformed or transiently transfected with said vector. Methods of transforming or transfecting animal or plant cells are well-known in the art. Various methods can be used to deliver DNA or RNA vector into the plant cell, including direct introduction of said vector into a plant cell by means of microprojectile bombardment, electroporation or PEG-mediated treatment of protoplasts (for review see: Gelvin, S. B., 1998, *Curr. Opin. Biotechnol.*, 9, 227-232; Hansen & Wright, 1999, *Trends Plant Sci.*, 4, 226-231). Plant RNA and DNA viruses are also efficient delivery systems (Hayes et al., 1988, *Nature*, 334, 179-182; Palmer et al., 1999, *Arch. Virol.*, 144, 1345-1360; Lindbo et al., 2001, *Curr. Opin. Plant. Biol.*, 4, 181-185). Said vectors can deliver a transgene either for stable integration into the genome/plastome of the plant (direct or *Agrobacterium*-mediated DNA integration) or for transient expression of the transgene ("agroinfiltration"). Similarly, animal cells may be electroporated, infected by viral vectors or transfected using Lipofectin.

Construction of the vectors for the expression process of the invention may be done according to standard procedures of molecular biology. Specific embodiments are outlined in the figures and in the examples section.

The invention comprises IRES elements identified or identifyable by the method of the invention. Particularly, the invention comprises an IRES element having a sequence of one of the sequences of FIG. 7 or FIG. 8 or an IRES-functional portion thereof.

The invention discloses for the first time IRES elements of plant origin. Such IRES elements are therefore comprised by the invention as are vectors containing such IRES elements. Preferably, an IRES contained in leaders of the *Arabidopsis* RPS18 gene family, notably in the leader of the RPS18C gene, or in leaders of genes homologous or orthologous thereto is excluded from the IRES elements of this invention.

Moreover, the invention comprises transgenic or transiently transfected eukaryotic cells transformed or transfected with a vector containing an IRES element according to the invention.

Furthermore, an RNA vector containing novel IRES RNA sequences, as well as a DNA vector containing DNA copies of novel IRES DNA sequences are described.

The invention is useful, as it allows one skilled in art to identify previously unknown natural translational elements with IRES activity. It allows to identify IRES elements that are more active than previously described ones. In addition, it allows the identification of IRES elements that are universal and active across different taxonomic kingdoms.

An essential advantage of the present invention is the possibility to express more then two genes in multicistronic cassettes in plant cells transiently or stably transformed (transgenic plants).

Another advantage of the present invention is the possibility to express more than two genes in multicistronic cassettes in human and mammalian cells transiently and stably transformed (transgenic animals).

Another advantage of the present invention is the possibility to express more than two genes in multicistronic cassettes in yeast cells.

A further advantage provided by the present invention is the possibility to construct virus vectors for expressing foreign genes via the novel IRESes of the invention in mammals and especially in humans.

BRIEF DESCRIPTION OF THE FIGURES

FIG. 3 depicts the nucleotide sequence of NtHSF-1 mRNA 5' leader (EMBL accession code AB014483, SEQ ID NO:4) (A) and cloning steps to produce pH-GFP-NtHSF-GUS (B). The PCR fragment was obtained using primers aagtaagcttggcacgaggctcccattaatatttc (SEQ ID NO:5) and ggaccatggctgtttttcccctgtatttctctg (SEQ ID NO:6) The initiation codon AUG is emphasised in italics.

FIG. 7 shows human 5'UTR nucleotide sequences as putative human IRESes from: Human poly (A)-binding protein (PABP) gene (SEQ ID NO:8); HSP70, testis variant (SEQ ID NO:9); HSP17 17 KD protein 3 (HSPB3, SEQ ID NO:10); HSP B3 (SEQ ID NO:11); HSPHDJ2 (SEQ ID NO:12); HSP 90 (SEQ ID NO:13); HSP70B (SEQ ID NO:14); and HSP86 (SEQ ID NO:15).

FIG. 8 shows plant 5'UTR nucleotide sequences as putative plant IRESes from: Tobacco 48-kD MAP kinase (SEQ DID NO:16); Tobacco MAP kinase (SEQ ID NO:17); N. tabacum GTP-binding protein (rac gene, SEQ ID NO:18); Oryza sativa GTP-binding protein OsRac1 (SEQ ID NO:19); N. tabacum poly (A)-binding protein (PABP) mRNA (SEQ ID NO:20); Plant heat shock protein mRNA 5'UTR Accession No. AB017273 (SEQ ID NO:21); Plant heat shock protein mRNA 5'UTR Accession No. AF005993 (SEQ ID NO:22); Plant heat shock protein mRNA 5'UTR Accession No. AF035460 (SEQ ID NO:23 Plant heat shock protein mRNA 5'UTR Accession No. AF074969 (SEQ ID NO:24); Plant heat shock protein mRNA 5'UTR Accession No. AF087640 (SEQ ID NO:25); Plant heat shock protein mRNA 5'UTR Accession No. AF133840 (SEQ ID NO:26); Plant heat shock protein mRNA 5'UTR Accession No. AF174433 (SEQ ID NO:27); and Plant heat shock protein mRNA 5'UTR Accession No. AF208051 (SEQ ID NO:28).

FIG. 9 depicts experimental steps of identification and isolation of a novel plant IRES from the 5'UTR of tobacco polyadenine-binding protein PABP mRNA. To produce pH-GFP-PABP-GUS, the PCR fragment was obtained using primers gcggcaagcttcgttgctgtcggagattttgtatc (SEQ ID NO:29) and cgcgccatggcaaatcaacacaaaaaaaacaaaaaaaaaataataaag (SEQ ID NO:30).

FIG. 10 depicts experimental steps of identification and isolation of novel plant IRES from the 5' UTR of tobacco 48K MAP kinase. To produce pH-GFP-48K MAPK-GUS, the PCR fragment was obtained using primers gcggcaagcttcaattccacatattcattg (SEQ ID NO:31) and cgcgccatggtttttttttttggaaaattcgtc (SEQ ID NO:32).

FIG. 11 shows nucleotide sequences of known animal and viral IRES elements from: EMCV IRES-containing mRNA 5'UTR (SEQ ID NO:33); Poliovirus IRES-containing mRNA 5'UTR (SEQ ID NO:34); Hepatitis C IRES-containing mRNA 5'UTR (SEQ ID NO:35); PSIV IRES-containing mRNA 5'UTR (SEQ ID NO:36); Human Apaf-1 IRES-containing mRNA 5'UTR (SEQ ID NO:37); Human c-myc IRES-containing mRNA 5'UTR (SEQ ID NO:38); Human BiP IRES-containing mRNA 5'UTR (SEQ ID NO:39); Human eIF4GII IRES-containing mRNA 5'UTR (SEQ ID NO:40); Rat fibroblast growth factor 2 IRES-containing mRNA 5'UTR (SEQ ID NO:41); Human vascular endothelial growth factor C IRES (SEQ ID NO:42); Rat riap3 IRES (SEQ ID NO:43); and Gtx homeodomain protein 5'UTR IRES (SEQ ID NO:44).

Figure 1:
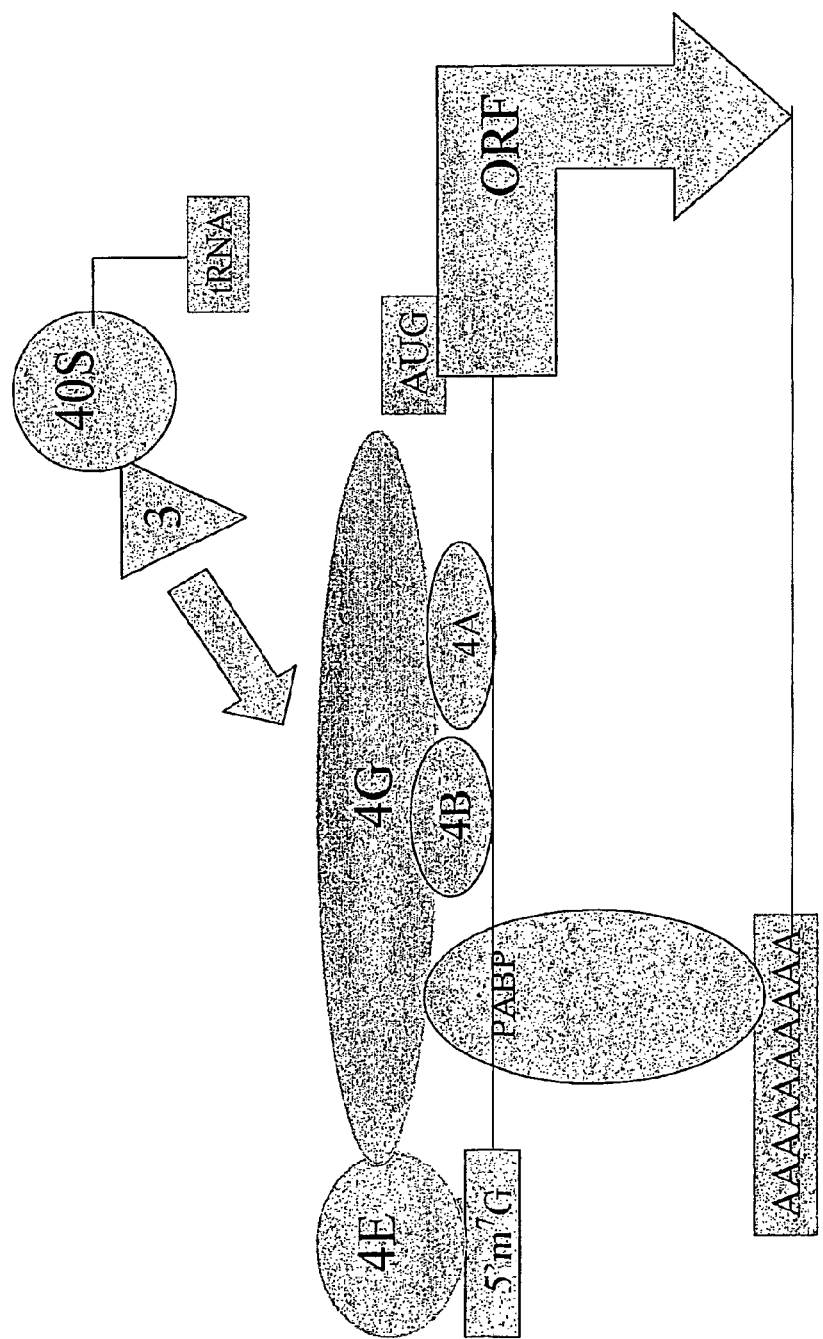
FIG. 1. Simplified model of canonical eukaryotic cap-dependent translation initiation. The eIF4E-eIF4G interaction targets the small ribosomal subunit to the 5'end of the mRNA. The eIF4G also interacts with Pab1p, eIF3, and the RNA helicase eIF4A to mediate the initiation process. ORF: open reading frame; PABP: poly (A)-binding protein, depicted herein interacting the poly (A) tail (SEQ ID NO:3) of an example mRNA.
Figure 2:
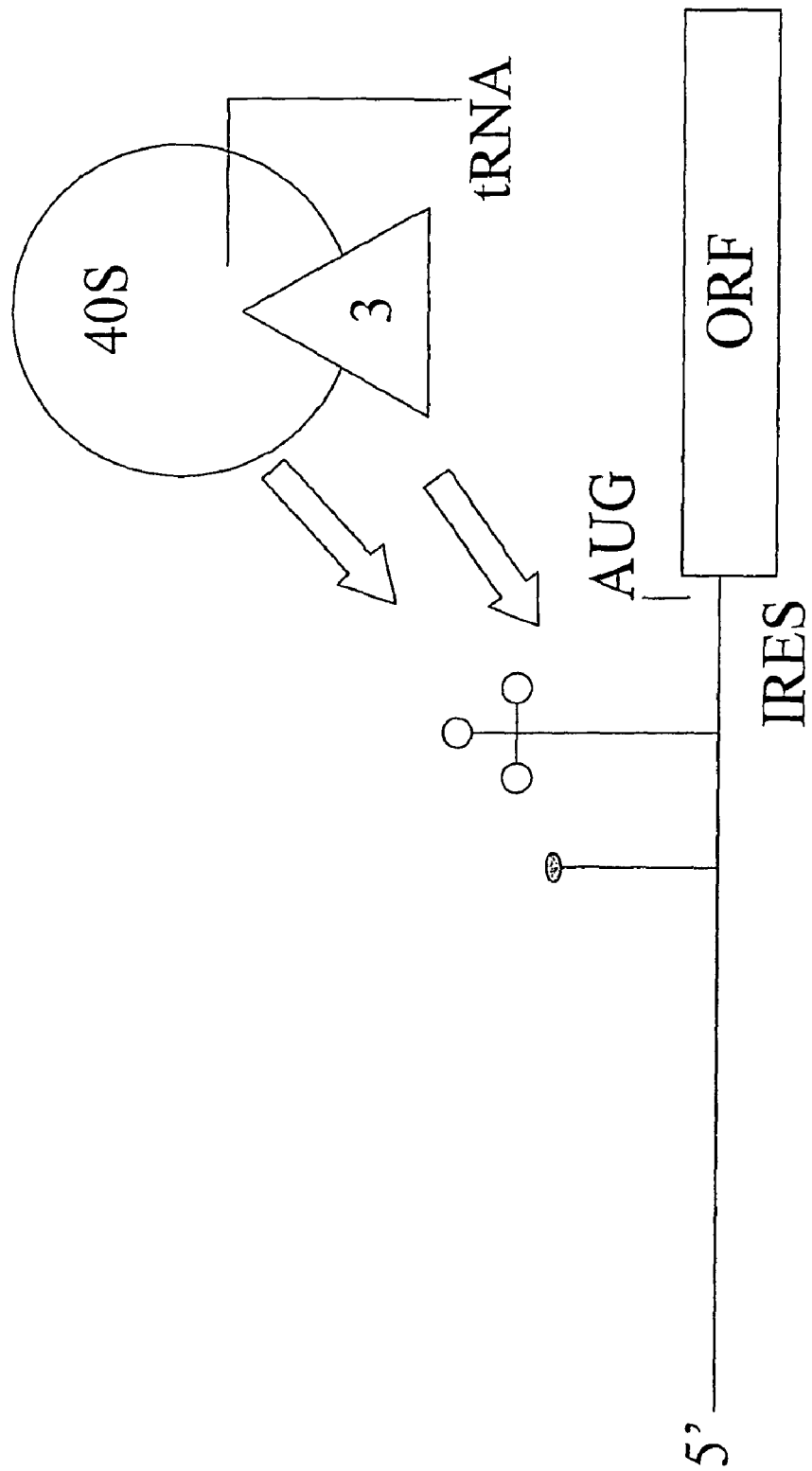
FIG. 2. Simplified model of the mechanism of ribosome recruitment to mRNA during hepatitis C virus IRES-mediated translation initiation. The IRES element bypasses the need for an eIF4E-eIF4G interaction by providing alternative means by which the ribosome is recruited to the mRNA. Arrows indicate the various direct interactions between IRES elements and the initiation 40S complex.

In the following, the invention will be further described using specific examples. Standard molecular biological techniques were carried out according to Sambrook et al (1989, Molecular Cloning: a Laboratory Manual. $2^{nd}$ ed. Cold Spring Harbor, N.Y.). All plasmids utilized in the invention can be prepared according to the directions of the specification by a person of ordinary skill in the art without undue experimentation employing materials that are readily available.

EXAMPLES

The goal of these example is to demonstrate approaches for revealing and creating earlier non-identified natural IRESes in 5'UTR eukaryotic mRNA sequences.

Example 1

Identification of a Novel IRES Sequence Isolated from NtHSF mRNA 5' UTR

Cloning Strategy

The 5'UTR of NtHSF-1 was selected by screening. It contains adenine-rich nucleotide blocks. It was cloned as outlined in FIG. 3 to produce transcriptional vector pH-GFP-NtHSF-GUS.

In vitro translational assays: WGE and RRL translation assay were carried out as described in Technical Bulletin No. 165 and No. 126, respectively, from Promega Corporation using the coupled transcription/translation systems of catalogue numbers L4140 and L4610, respectively. Alternatively, a conventional RRL system from Promega, catalogue number L4960 (Technical Manual No. 232) was employed. Linear H-GFP-GUS vectors having potential IRES elements inserted between GFP and GUS were transcribed using the T7 promoter/RNA polymerase system. RNA transcripts were precipitated with LiCl, dissolved in water, reprecipitated with ethanol. RNA concentrations were measured by spectrophotometry and 5 :g of each transcript was taken for 25-µl in vitro translation sample GFP and GUS expression were detected by autoradiography.

The transient assay system from plant protoplasts. The following procedures of protoplast preparation and transfection were used: (i) The protoplasts were isolated from $N.$ $tabacum$ (cv. W38) leaves as described (Saalbach et al., 1996 Plant Physiol. 112, 975-985). Aliquotes of $4 \times 10^5$ protoplasts were transfected with 30 µg of pFF19-based dicistronic DNA constructs "GFP-spacer-GUS" and incubated for 36 hours at 25° C. in the dark. GUS activity was measured as relative light units (RLU). GUS activity was determined according to (Jefferson 1987 Plant Mol. Biol. Rep. 5, 387-405) using MUG. For each experiment background GUS activity associated with non-transfected protoplasts was subtracted. Protein concentrations were estimated using the Bio-Rad protein assay kit based on the method of Bradford (1976 Anal. Biochem. 72, 248-254). GFP expression was detected by western-blot analysis using monoclonal mouse antibodies (Boehringer Mannheim No. 1814460) according to the manufacturer's manual. GFP amounts in western-blot bands were calculated using Bio-Rad Quality-One software.

Transfection of HeLa cells using Vaccinia Virus and 77 Promoter Containing Plasmids, Encoding for GUS HeLa cell monolayers were grown on 3.5 cm Petri dishes in Dulbecco's modified minimal essential medium supplemented with 10% heat-inactivated fetal calf serum, and 100 units/ml streptomycin and penicillin. Virus stocks of modified vaccinia virus Ankara (MVA), expressing bacteriophage T7 RNA polymerase gene were made according to usual methods. HeLa cell dishes that were 80-90% confluent were infected with virus using 30-40 pfu/cell. After a 45 min absorption period the cells were washed and transfected using Opti-MEM (Life Technologies, Inc.) plasmid DNA and Lipofectin (life Technologies, Inc.). A transfection mixtures of 2 µg DNA in 5 µl Lipofectin was used for a 3.5 cm plate. For each construct, 6 plates were used in each experiment. Cells were incubated at 37° C. for 6 h. After incubation the media was removed, cells were washed twice with PBS and lysed directly on the plate in 250 µl lysis buffer (100 mM $KHPO_3$ pH7.8, 0.2% Triton X-100, 0.5 mM DTT) for 10 minutes. The lysate was collected, clarified by centrifugation at 2000 g for 10 minutes and stored at −70° C. GUS activity was detected in 20 µl of lysate using GUS Light™ reagent system (Tropix, MA, USA) according to the manufacturer's protocols.

Results

Figure 4:
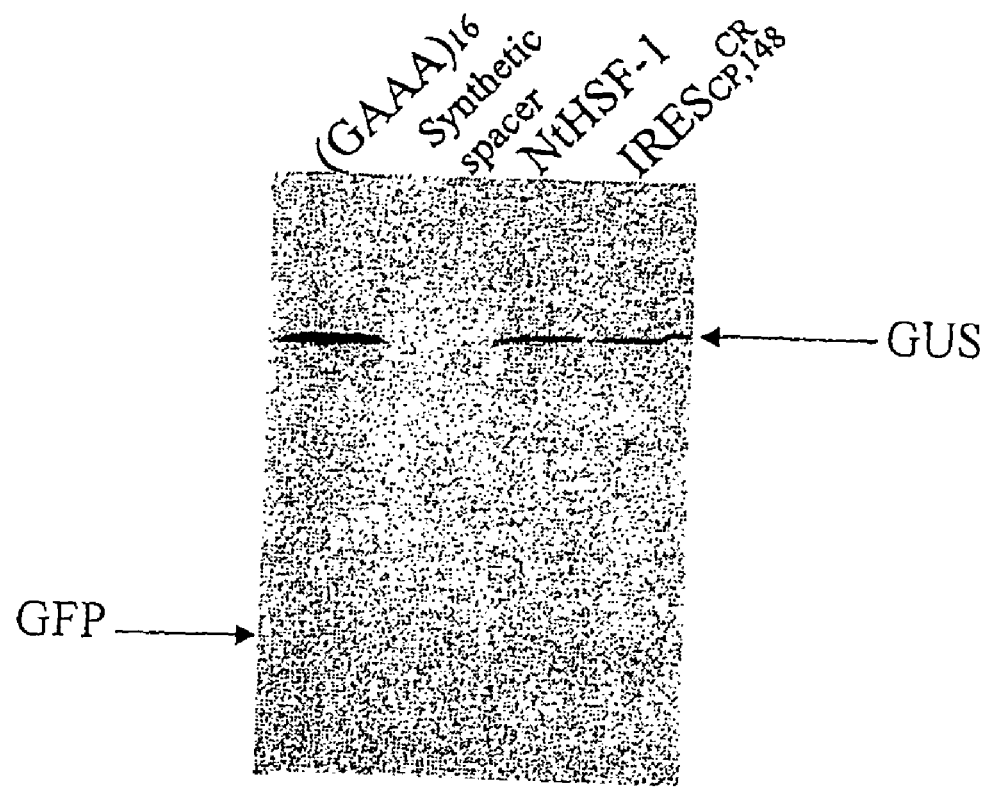
FIG. 4 shows an autoradiograph of proteins translated in WGE by H-GFP-GUS containing (i) 36-nt artificial sequence (spacer) gcgugggcggcgugggcguuuguucuuuguuugacc (SEQ ID NO:7), (ii) 453-nt NtHSF-1 mRNA 5' leader, (iii) $(GAAA)_{16}$ (SEQ ID NO:1) and $IRES_{CP,148}^{CR}$ as intercistronic spacers. Arrows indicate the position of GUS and expected positions of GFP.
Figure 5:
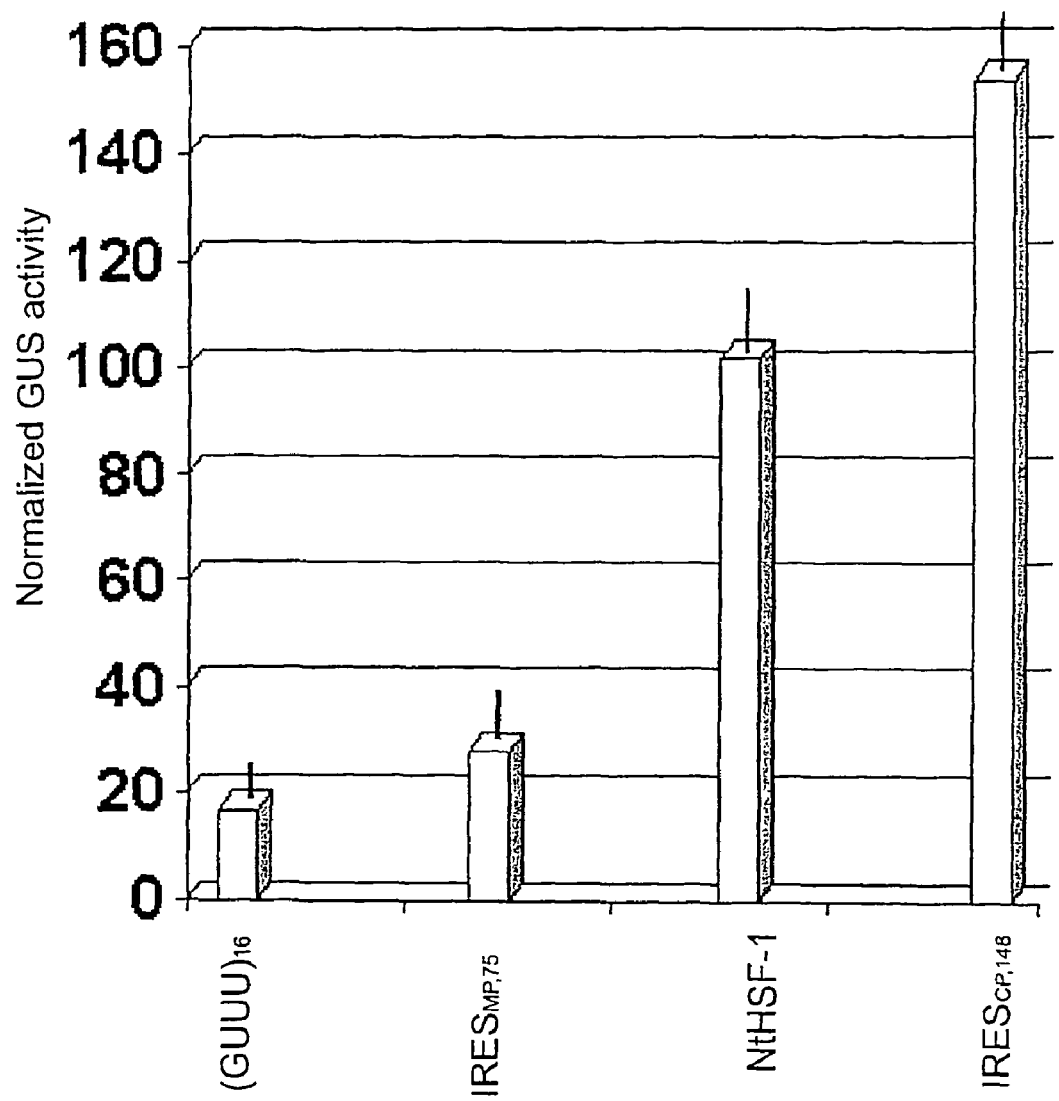
FIG. 5 shows a diagram of GUS gene expression in tobacco protoplasts transfected with 35S-based hairpin-less bicistronic GFP-GUS constructs containing the nucleotide sequences indicated under the diagram bars. GUS activity values of each transgenic plant were normalized to the GFP content in the same protoplast sample determined by densitometry of GFP bands from Western blots. At least three independent experiments were used for the calculation of average values and standard errors depicted as vertical bars.
Figure 6:
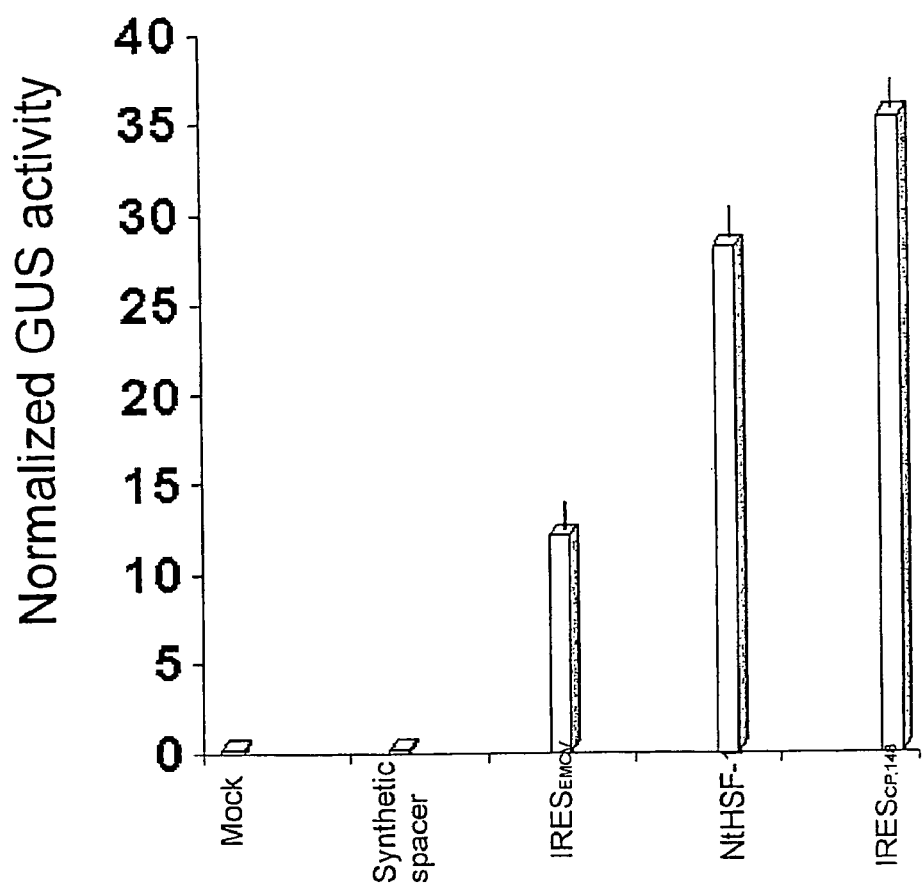
FIG. 6 shows a diagram of GUS gene expression in HeLa cells transfected with bicistronic T7-based construct H-GFP-GUS. GUS values were normalised to protein contents of samples. At least three independent experiments were used for the calculation of average values and standard errors depicted as vertical bars.

The 453-nt 5' leader of Nicotiana tabacum heat shock factor 1 (NtHSF-1, EMBL nucleotide database accession code AB014483) was isolated from a tobacco cDNA bank and was used as an intercistronic spacer in bicistronic construct H-GFP-GUS which was tested in WGE and RRL in vitro translational systems (FIG. 4) and also in tobacco protoplasts (FIG. 5) and HeLa cells (FIG. 7). FIG. 4 shows the results of translation in WGE bicistronic construct H-GFP-GUS containing the NtHSF-1 5' leader in comparison with the 36-nt artificial sequence gcgugggcggcgugggcguuuguucuuu-guuugacc (SEQ ID NO:7) taken as a control, and $(GAAA)_{16}$ (SEQ ID NO:1) and $IRES_{CP,148}{}^{CR}$ taken as a positive control. It can be seen that the NtHSF-1 leader provided efficient expression of the GUS gene in WGE although expression of 5'-proximal gene (GFP) was blocked by a stable hairpin structure. Analogous results were obtained with the RRL system (data not shown). To confirm the results obtained in vitro, we tested the NtHSF-1 leader on IRES activity in plant tobacco protoplasts and human HeLa cells. The results presented in FIGS. 5 and 6, respectively, shows that the NtHSF-1 leader possessed IRES activity comparable to $IRES_{CP,148}{}^{CR}$ in both types of eukaryotic cells. Thus, it was concluded that the NtHSF-1 leader, like $IRES_{CP,148}{}^{CR}$, possesses cross-kingdom activity and can be considered as an IRES sequence ($IRES^{NtHSF-1}$).

The results demonstrate that application of the seerching criterial of the present invention allows to identify IRES elements in 5' leaders of a eukaryotic mRNA.

Example 2

Identification of a Novel IRES Sequence Isolated from Tobacco Poly(a) Binding Protein mRNA 5'UTR An analysis of human and plant mRNA 5'UTR according to the criteria of the invention revealed other sequences with a high chance of having IRES activity (FIGS. 7 and 8). We selected from this list of sequences 5'UTR of tobacco poly(A)-binding protein (PABP) to confirm the efficiency of our methodology of prediction and identification of novel IRES sequences.

Cloning Strategy: The Approach for PABP IRES Isolation is Described in FIG. 9.

The obtained DNA constructs were linearized with NotI enzyme and transcribed with T7-polymerase. RNA transcripts were precipitated with LiCl, dissolved in water, and reprecipitated with ethanol. RNA concentrations were measured by spectrophotometry and 5 µg of each transcript was taken for 25-µl in vitro translation sample (RRL, Promega).

The results presented in Table 3 show that the PABP 5'UTR was able to direct efficient GUS gene expression in the RRL system. Additionally, PABP 5'UTR provided GUS gene expression in HeLa cells as well (Table 4).

Example 3

Identification of a Novel IRES Sequence Isolated from Tobacco 48K MAP Kinase 5'UTR mRNA The goal of this example is to confirm the validity of our approach for searching novel plant IRESes. We selected from the list of putative IRESes (FIG. 8) the 5'UTR of tobacco 48K MAP kinase (MAPK) to confirm the efficiency of our methodology of prediction and identification of novel IRES sequences.

Cloning Strategy: The Approach for 48K-MAPK IRES Isolation is Described in FIG. 10.

The obtained DNA constructs were linearized with NotI enzyme and transcribed with T7-polymerase. RNA transcripts were precipitated with LiCl, dissolved in water, and reprecipitated with ethanol. RNA concentrations were measured by spectrophotometry and 5 µg of each transcript was taken for 25-µl in vitro translation sample (RRL, Promega).

The results presented in Table 5 show that the 48K-MAPK 5'UTR is capable of directing efficient GUS gene expression in RRL.

TABLE 1

Virus IRESes

| Virus type | Virus | IRES localization | Reference |
|---|---|---|---|
| Animal RNA Viruses ||||
| Picornaviruses | Poliovirus (PV) | 5'UTR | Pelletier & Sonenberg (1988). Nature 334, 320-325 |
| | Encephalomyocarditis virus (EMCV) | 5'UTR | Jang et al. (1988) J. Virol. 62, 2636-2643 |
| | Foot-and-mouth disease virus (PMDV) | 5'UTR | Kuhn et al. (1990) J. Virol. 64, 4625-4631 |
| Flavivirus | Hepatitis C virus | 5'UTR | Reynolds et al. (1995). EMBO J. 14, 6010-6020 |
| Pestivirus | Classical swine fever virus (CSFV) | 5'UTR | Pestova et al. (1998). Genes and Devel. 12, 67-83 |
| Retrovirus | Murine Leukaemia virus (MLV) | 5'UTR | Berlioz & Darlix (1995). J. Virol. 69, 2214-2222 |
| Lentivirus | Simian immunodeficiency virus (SIV) | 5'UTR | Ohlmann et al., (2000). J. Biol. Chem. 275, 11899-11906. |
| Insect RNA virus | Cricket paralysis virus | Two IRESes (5'UTR and internal) | Wilson et al. (2000). Mol. Cell. Biol. 20, 4990-4999 |
| | *Plautia stali* intestine virus (PSIV) | Internal | Sasaki & Nakashima (1999). J. Virol. 73, 1219-1226 |
| Plant RNA Viruses ||||
| Tobamoviruses | Crucifer infecting tobamovirus (crTMV) | Two IRESes (both internal) | Ivanov et al. (1997). Virology 232, 32-43; Skulachev et al. (1999). Virology 263, 139-154 |
| | Tobacco mosaic virus (TMV) | internal | Skulachev et al. (1999). Virology 263, 139-154 |
| Potexvirus | Potato virus X (PVX) | internal | Hefferon et al. (1997). J. Gen. Virol. 78, 3051-3059 |
| Potyvirus | Tobacco etch virus (TEV) | 5'UTR | Carrington & Freed (1990). J. Virol. 64, 1590-1597 |
| | Turnip mosaic virus (TuMV) | 5'UTR | Basso et al. (1994). J. Gen. Virol. 75, 3157-3165 |
| Comovirus | Cowpea mosaic virus (CpMV) | 5'UTR | Verver et al. (1991). J. Gen. Virol. 72, 2339-2345 |

TABLE 2

Eukaryotic cellular mRNA IRESs

| Gene type | Gene | IRES localization | Reference |
|---|---|---|---|
| Animal cellular mRNA ||||
| Translation intiation factors | EIF4G | 5'UTR | Johannes & Sarnow (1998). RNA 4, 1500-1513 |
| | DAP5 | 5'UTR | Henis-Korenbit et al. (2000). Mol. Cell. Biol. 20, 496-506 |
| Growth Factors | Vascular endothelial growth factor (VEGF) | 5'UTR | Huez et al. (1998) Mol. Cell. Biol. 18, 6178-6190 |

TABLE 2-continued

Eukaryotic cellular mRNA IRESs

| Gene type | Gene | IRES localization | Reference |
|---|---|---|---|
| | Fibroblast growth factor 2 (FGF-2) | 5'UTR | Creancier et al. (2000). J. Cell. Biol. 150, 275-281 |
| | Mnt | 5'UTR | Stoneley et al. (2001). Oncogene 20, 893-897. |
| | Platelet-derived growth factor B (PDGF B) | 5'UTR | Bernstein et al. (1997). J. Biol. Chem. 272, 9356-9362 |
| Homeotic genes | Antennapedia | 5'UTR | Oh et al. (1992) Genes & Devel. 6, 1643-1653 |
| Survival proteins | X-linked inhibitor of apoptosis (XIAP) | 5'UTR | Holcik & Korneluk (2000). Mol. Cell. Biol. 20, 4648-4657 |
| | Apaf-1 | 5'UTR | Coldwell et al. (2000). Oncogene 19, 899-905. |
| Miscellaneous | BiP | 5'UTR | Macejak & Sarnow (1991). Nature 353, 90-94 |
| | Dendrin, neurogranin, α-subunit of the calcium-calmodulin-dependent kinase II, ARC, MAP2 | 5'UTR | Pinkstaff et al. (2001). Proc. Natl. Acad. Sci. USA 98, 2770-2775 |
| | Connexin-32 | 5'UTR | |

Plant cellular mRNA

| Gene type | Gene | IRES localization | Reference |
|---|---|---|---|
| Heat shock Protein | *Nicotiana tabacum* heat shock factor 1 (NtHSF-1) | 5'UTR | This application |
| Translation intiation factor | *Nicotiana tabacum* Poly(A)-binding protein (PABP) | 5'UTR | This application |

TABLE 3

GUS gene expression in RRL directed by PABP 5' UTR in bicistronic construct.

| Construct | 4MU fluoresc. after 30' (RLU) | 4MU fluoresc. after 60' (RLU) |
|---|---|---|
| hGFP-PAB5'UTR-GUS | 158233 | 271943 |
| hGFP-IREScp148-GUS | 208499 | 358621 |
| NoRNA | 643 | 674 |

TABLE 4

GUS expression in HeLa cells directed by PABP 5' UTR (all activities in RLU).

| Construct | GUS after 30' | GUS after 60' |
|---|---|---|
| HGFP-PABP 5'UTR-GUS | 9397 | 18639 |
| | 8342 | 16765 |
| | 10309 | 20707 |
| HGFP-IREScp-GUS | 237953 | 427810 |
| | 232171 | 437064 |
| | 257613 | 473244 |
| GFP-IREScp-GUS | 273731 | 508842 |
| | 236659 | 445389 |
| Mock (approx.) | 400 | 650 |

TABLE 5

GUS gene expression in RRL directed by 48K MAPK 5'UTR in bicistronic construct.

| Construct | 4MU fluoresc. after 30' (RLU) |
|---|---|
| hGFP-48K MAPK5'UTR-GUS | 184235 |
| hGFP-IREScp148-GUS | 190210 |
| No RNA | 1567 |

The invention claimed is:

1. A process of expressing a nucleotide sequence of interest in eukaryotic cell(s), wherein the process comprises introducing into said cell(s) a vector comprising said nucleotide sequence of interest operably linked to an upstream IRES element of eukaryotic origin, wherein the IRES element comprises a nucleotide sequence selected from the group consisting of SEQ ID NO:8, SEQ ID NO:13, SEQ ID NO:15, SEQ ID NO:18, and SEQ ID NO:20, whereby said nucleotide sequence of interest is translated cap-independently by way of said IRES element.

2. The process of claim 1, wherein said nucleotide sequence of interest is expressed as part of a bicistronic or a polycistronic mRNA.

3. The process of claim 1, wherein the IRES element is of mammalian origin.

4. The process of claim 1, wherein said eukaryotic cell is a plant cell.

5. The process of claim 1, wherein said eukaryotic cell is an animal cell.

6. The process of claim 1, wherein said eukaryotic cell is a yeast cell.

7. A process of expressing a nucleotide sequence of interest in eukaryotic cell(s), wherein the process comprises introducing into said cell(s) a vector comprising said nucleotide sequence of interest operably linked to an upstream IRES element of plant origin, wherein the IRES element comprises SEQ ID NO:20, whereby said nucleotide sequence of interest is translated cap-independently by way of said IRES element.

8. A process of expressing a nucleotide sequence of interest in eukaryotic cell(s), wherein the process comprises introducing into said cell(s) a vector comprising said nucleotide sequence of interest operably linked to an upstream IRES element, wherein the IRES element comprises SEQ ID NO:20, whereby said nucleotide sequence of interest is translated cap-independently by way of said IRES element.

* * * * *